(12) United States Patent
Pellegretti et al.

(10) Patent No.: US 10,641,879 B2
(45) Date of Patent: May 5, 2020

(54) SYSTEMS AND METHODS FOR DISTORTION FREE MULTI BEAM ULTRASOUND RECEIVE BEAMFORMING

(71) Applicant: ESAOTE SpA, Genoa (IT)

(72) Inventors: Paolo Pellegretti, Genoa (IT); Theodorus Franciscus Mulder, Geulle (NL)

(73) Assignee: Esaote S.p.A., Genoa (IT)

( * ) Notice: Subject to any disclaimer, the term of this patent is extended or adjusted under 35 U.S.C. 154(b) by 324 days.

(21) Appl. No.: 15/869,367

(22) Filed: Jan. 12, 2018

(65) Prior Publication Data
US 2018/0203103 A1 Jul. 19, 2018

(30) Foreign Application Priority Data
Jan. 19, 2017 (EP) .................................... 17152207

(51) Int. Cl.
*G01S 7/52* (2006.01)
*G01S 15/89* (2006.01)
(Continued)

(52) U.S. Cl.
CPC ...... *G01S 7/52077* (2013.01); *G01S 7/52028* (2013.01); *G01S 7/52095* (2013.01);
(Continued)

(58) Field of Classification Search
CPC ............. G01S 7/52077; G01S 15/8977; G01S 7/52028; G01S 15/8915; G01S 7/52095; G10K 11/346
See application file for complete search history.

(56) References Cited

U.S. PATENT DOCUMENTS 5,685,308 A 11/1997 Wright et al.
5,921,932 A * 7/1999 Wright ................ G01S 15/8988
600/447
(Continued)

FOREIGN PATENT DOCUMENTS

EP 3352166 A1 * 7/2018 ......... G01S 7/52095

OTHER PUBLICATIONS

Powers J. E. et al., "Ultrasound Phased Array Delay Lines Based on Quadrature Sampling Techniques", IEEE Transactions on Sonics and Ultrasonics, IEEE, US, vol. 27, No. 6, Nov. 1, 1980, pp. 287-294, XP011404338.
(Continued)

*Primary Examiner* — Daniel Pihulic
(74) *Attorney, Agent, or Firm* — Dickinson Wright PLLC

(57) ABSTRACT

The present disclosure relates to an ultrasound multi line dynamic receive focusing beam former that is part of an ultrasound system, where the beam former of the present invention resolves conceptually the, in the prior art dynamic receive focusing beam formers, by fundament, internally generated distortions, which (in the prior art), become internally generated by the beam former process itself. These distortions within prior art beam formers, typically compromises, to some degree, the ability of accurate detections after the dynamic receive focusing beamforming. The present invention advantage is an ultrasound system capable of very accurate focusing selectivity with a high dynamic range, and very low signal distortion, therefore capable of, for example, a clear detection of harmonics and super harmonics, due to the fundamentally absence of internal distortion-generation. The scope is to resolve several, in prior-art, mentioned issues above, to provide computational efficient systems and methods capable of detecting the applications-features, very accurate and at high speed, uti-
(Continued)

lizing the distortion free ultrasound Retrospective Transmit focus capable, multi-line dynamic receive focusing beamforming, which can be realized in hardware or software, wherein instead of 1d time domain processing, also 1d frequency domain processing might be utilized, suitable for other modalities that need longer detection lengths (like coding in Tx sequences).

19 Claims, 14 Drawing Sheets

(51) Int. Cl.
G10K 11/34 (2006.01)
A61B 8/08 (2006.01)

(52) U.S. Cl.
CPC ...... *G01S 15/8915* (2013.01); *G01S 15/8977* (2013.01); *G10K 11/346* (2013.01); *A61B 8/5207* (2013.01); *A61B 8/5269* (2013.01)

(56) References Cited

U.S. PATENT DOCUMENTS

| | | | |
|---|---|---|---|
| 5,928,152 A * | 7/1999 | Wright | G01S 15/8988 600/447 |
| 6,029,116 A * | 2/2000 | Wright | G01S 7/52023 702/32 |
| 2007/0229336 A1 | 10/2007 | Liu et al. | |
| 2013/0079639 A1 | 3/2013 | Hoctor et al. | |
| 2015/0045666 A1 | 2/2015 | Lin | |
| 2016/0228092 A1 | 8/2016 | Kim et al. | |
| 2016/0262729 A1 | 9/2016 | Srinivasan et al. | |
| 2018/0003811 A1 * | 1/2018 | Pellegretti | A61B 8/5207 |
| 2018/0203103 A1 * | 7/2018 | Pellegretti | G01S 15/8977 |

OTHER PUBLICATIONS

European Search Report dated Jul. 7, 2017 which issued in European Patent Application No. EP 17152207.

* cited by examiner

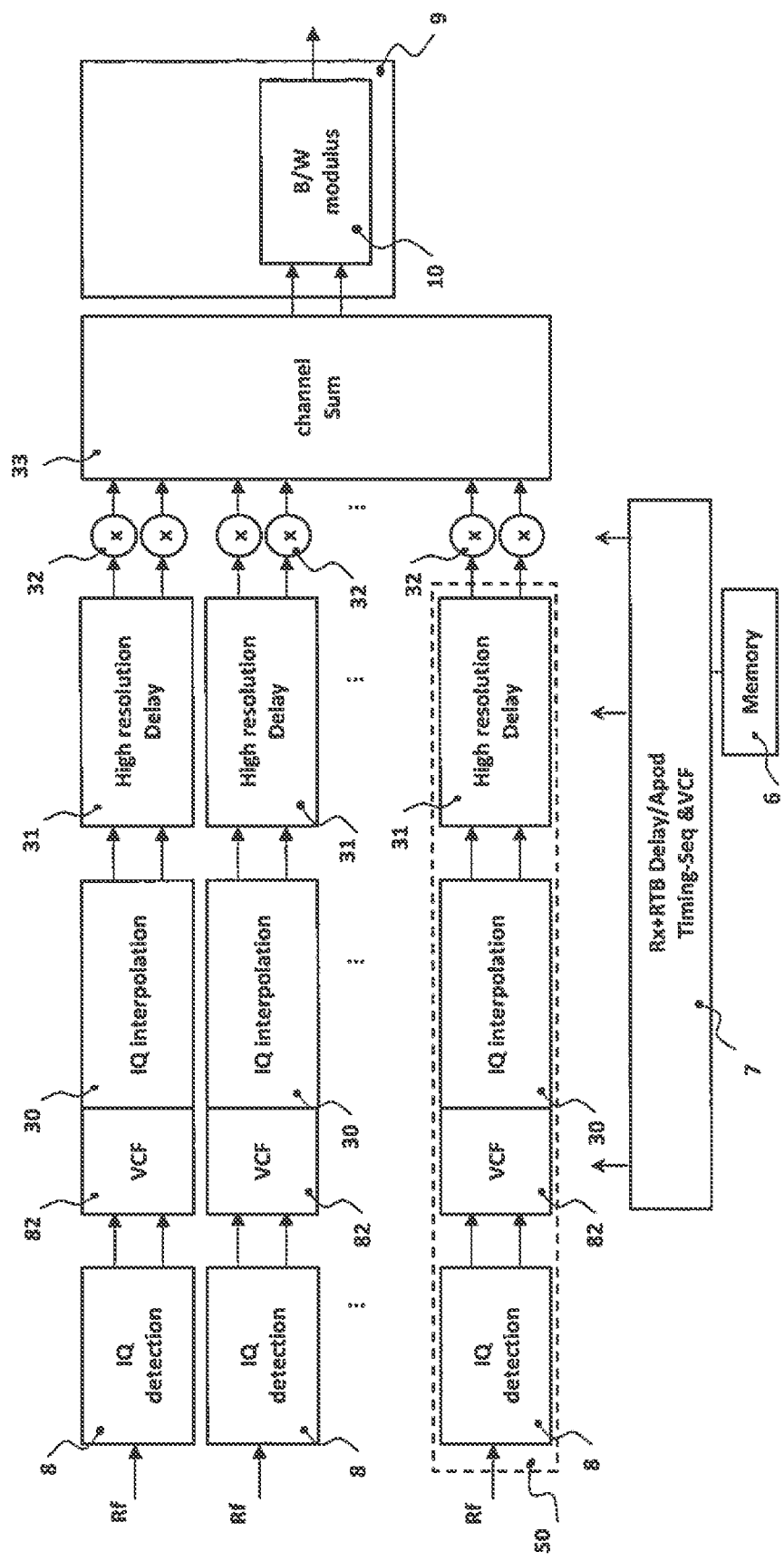

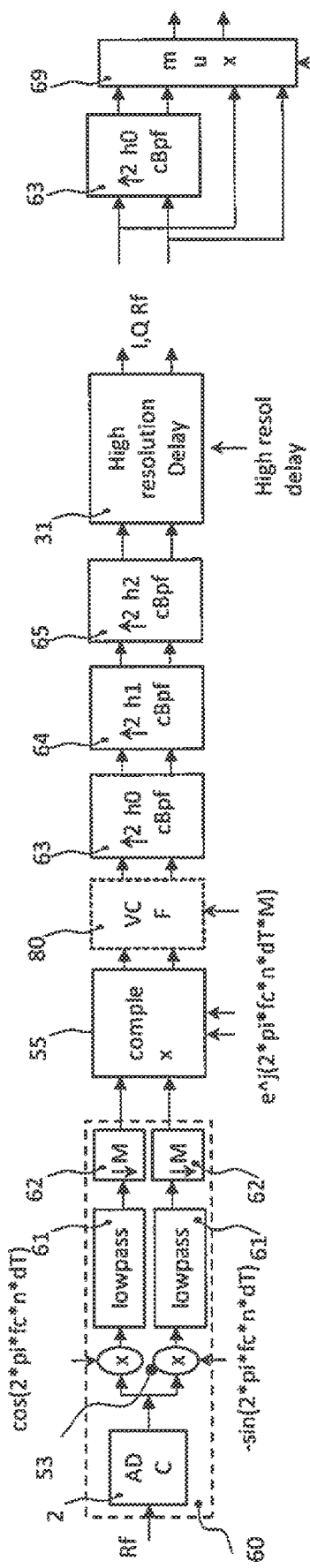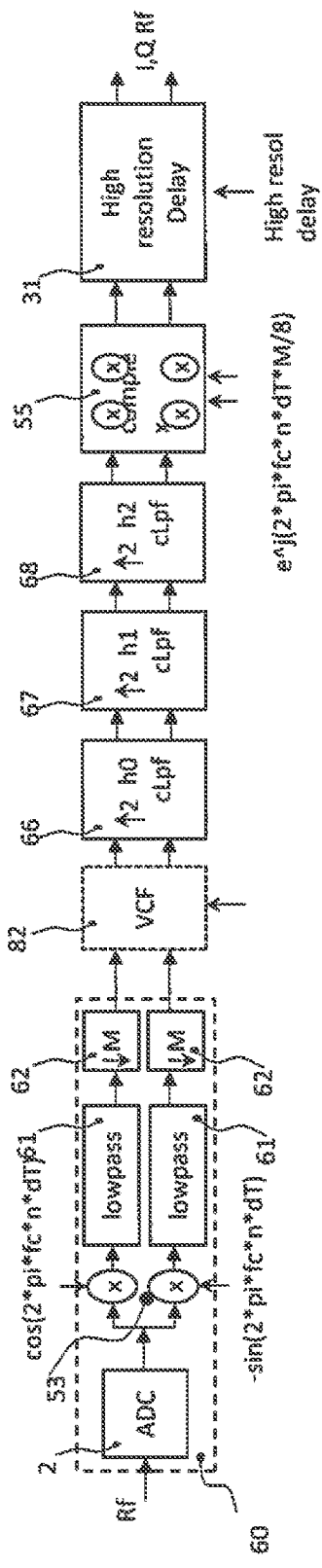
Fig. 4c
Fig. 4d
Fig. 4e

SYSTEMS AND METHODS FOR DISTORTION FREE MULTI BEAM ULTRASOUND RECEIVE BEAMFORMING

BACKGROUND OF THE INVENTION

Ultrasound systems exist today that utilize a variety of techniques for processing ultrasound signals to generate information of interest. For example, a variety of techniques exist today for performing beamforming upon ultrasound receive signals. One approach to beamforming performs Rf-beamforming upon analog or digitalized receive signals. Another approach to beamforming performs baseband beamforming upon digitalized receive signals. In the technical field of diagnostic, ultrasound imaging it is common practice to perform receive focusing in a dynamic way during the reception of the ultrasound signals, this realizes a certain sharpness over a wider depth range. However, in a dynamic receive focusing delay and sum beamforming technique, the signal delays are dynamically changing during the reception, as a result internal signal distortions become generated by the way of signal processing of the beamforming itself.

It is known in the technical field of diagnostic, ultrasound imaging, that the coherent summation process in the beamforming needs accurate fine-delay, realizing, low sidelobe-levels and good focus selectivity, and therefore high dynamic range. Several techniques are proposed for the fine delay, as interpolation and/or phase rotation. However, as phase rotations are computationally more effective, the phase rotation is not a true fine delay of the total-signal, but only a delay of the carrier part of the signal, the envelope of the signal is not fine delayed, this also results in the generation of signal-distortions in the beamforming. Correct fine delay of signals can only be performed by means of interpolation. However, it needs a high performance means of interpolation quality, to prevent signal-distortions produced by the interpolation. High performance interpolation in the beamforming requires a considerable computational burden. Poly phase interpolation is computationally more effective, but needs, in this case of ultrasound beamforming, a fine-delay control in each receive signal path, as a result, the signal processing of all the beamforming elements together becomes, at the end, very computationally intensive. Another solution is to use straight forward up-sample interpolation, which is computationally more intensive, but it can be split. The up-sampling part can be realized during the fine delay control in each receive signal path of the beamforming, and the computationally intensive filter-part of the interpolation, can be placed after the coherent summing of the beamforming. As a result it becomes a very computationally effective beamforming solution. However, also here, internal signal distortions become generated by the changing fine delay at the up-sample control stages, of this type of dynamic receive focusing beamforming.

Also common practice is the processing of multiple dynamic receiving focusing ultrasound beams, related to one ultrasound transmit event, this technique provides faster image frame-rates, but at the expense of lateral artifacts or loss of lateral sharpness. Synthetic Aperture and Retrospective Transmit Focusing in the technical field of diagnostic ultrasound imaging, provides some means to restore this kind of problems. As a consequence of these techniques, the ultrasound beamforming needs to provide a higher number of multiple dynamic receiving focusing ultrasound beams, with additional control of dynamic signal delays and apodizations. To realize a dynamic receive focusing multi-beam beamforming with a high performance fine-delay interpolation quality it becomes very computationally intensive.

Depth depending tracking filters, in here named as VCF, are also common practice in the technical field of diagnostic ultrasound imaging. During the reception of the ultrasound signals during the increasing time, relating to the reception of signals from the object of increasing depth, the signals become attenuated related to depth, and ultrasound frequency. The higher frequencies become more attenuated over depth then the lower frequencies, the effect is that at deeper locations the higher frequencies are severely attenuated, the high frequencies become hidden in the noise. To improve the SNR, depth depending tracking filters (VCF) are utilized, whereof, in traditional ultrasound systems the VCF is positioned after the beamforming. The presence of any kind of depth depending tracking filters after the traditional beamforming, will also result in internal signal distortion as a result of the traditional manner of delay and sum beamforming.

Further in the technical field of diagnostic ultrasound imaging, several other advanced techniques are utilized, like coded-transmission, or pulse-compression techniques, and several means of frequency-domain beamforming techniques are known.

With the coded-transmission, or pulse compression, the means of detection associated with these types of transmission, typically utilize some means of correlation techniques. The length, in time, of the used correlation template can be very long, resulting in filters with a large number of filter-taps.

The frequency-domain beamforming is mostly realized by some means of 2d spectral estimation, in combination with some means of interpolation in the 2d-frequency domain. The frequency-domain beamforming of other than linear array, is still very complex.

It is the scope of the present disclosure to resolve several mentioned issues above, and to provide systems and methods for a distortion free ultrasound multi-line dynamic focusing beamforming.

A further object of the present disclosure is to provide for a method and an ultrasound system allowing a distortion free ultrasound multi-line dynamic focusing beamforming having further Retrospective Transmit focus capability, in a computationally effective manner.

Another object is to provide for a method and an ultrasound system allowing a distortion free ultrasound multi-line dynamic focusing beamforming allowing fine delay interpolation with reduce computational burden.

BRIEF SUMMARY OF THE PRESENT INVENTION

The term I,Q-detection is used in the description: I,Q-detection is a filter to obtain complex receive signals having in-phase (I) and quadrature (Q) components. The I,Q-detection might be, a bandpass-filter and Hilbert-filter, or a complex-band pass filter, or an I/Q-demodulator with filters. Further it can be named that I,Q-detection relates to the estimations of the I,Q-vectors. And it can be named that with the used term I,Q Rf, is meant an I,Q version of the original received Rf-signals, with its spectral content around the transmitted center Rf-frequency fc.

The present invention will perform, on the ultrasounds probe elements original received signals s(t, Elm), I/Q-detections and I/Q interpolations, prior to the multi-line dynamic receive focusing delay and sum beamforming, where the beamforming is utilizing I/Q-Rf signals. A means of an cascade I,Q interpolation, and a pre-compute scheme is used to provide a very computational efficient way of I,Q interpolation for the delay-stages where output decimation will be used in combination with multi-line beamforming. Further, the invention relates to a corresponding multi-line hardware or software beam former system. Several embodiment examples will be described, in the detailed description section, wherein each embodiment example will utilize the fundamental distortion free solution concept as will briefly be described hereafter, after first giving an explanation of the problem of the presence of internal signal distortion-generation within traditional delay and sum beamforming in the following paragraph.

Internal Distortion is Generated in Traditional Delay and Sum Beamforming:

A traditional delay and sum beam-former, can be described as (I), (for simplicity apodization weighting is omitted).

$$BF(t) = \sum_{Elm} s(t - \tau del(t, Elm), Elm) \quad (1)$$

After the traditional beam-former a detection is performed, mostly an I,Q-detection of some sort is used to estimate I,Q-vectors containing amplitude and phase. The I/Q-detection process is a convolution over a certain detection window time-span 'τw', with a hdet(t) as effective complex-impulse response. This I,Q-detection after the beamforming can be formalized as:

$$BFD(t) = BF(t)*hdet(t) = \int_{-\tau w/2}^{\tau w/2} BF(t-\tau) \cdot hdet(\tau) \cdot d\tau$$

Formalization of the traditional delay and sum beamforming, with the I/Q-detection included, follows by substitution of the previous formulas, with as a result (2).

$$BFD(t) = \int_{-\tau w/2}^{\tau w/2} \sum_{Elm} s(t - \tau - \tau del(t - \tau, Elm), Elm) \cdot hdet(\tau) \cdot d\tau \quad (2)$$

Since the beam-formers delay portion . . . τdel( . . . −τ, . . . ) changes nonlinear with the differential variable dr, it causes the time inside s(t−τdel(t, Elm), Elm) (1) to become nonlinear, which causes the, on the probe elements original received signals s(t, Elm), to be altered into nonlinear distorted signal versions s(t−τdel(t, Elm), Elm). Thereof the traditional beam-former is afflicted with an internal signal distortion that becomes generated by the way of signal processing of the beam-former itself. It is due to the receive focus delay τdel(t, Elm), that changes overtime, in combination with the fact that an estimation of an I,Q-vector, can only be found by means of an integral over a certain detection-time span 'τw', that the estimated I,Q-vectors are affected by the distortion of s(t−τdel(t, Elm), Elm), therefor as a result the detected I,Q signal is also afflicted with distortion. Regardless of whether the signal processing is performed in continuous time or in (a more practical) discrete time, the usage of τdel(t, Elm) causes the beam former to be afflicted with internal signal distortion. Even with the application of interpolation with very accurate delay time- and amplitude-resolution, this beam-former type will still be afflicted with internal signal distortions.

Solution of Present Invention to Resolve Internal Generated Distortion:

The beam-former of this invention resolves the problem of the beamforming being afflicted with an internal signal distortion that becomes generated by the way of signal processing of the beamforming process itself. The beamforming of this invention starts with an I,Q-detection by means of an convolution of each, on the probe elements original received signals s(t, Elm), with an effective complex-impulse response hdet(t).

$$D(t, Elm) = s(t, Elm) * hdet(t)$$
$$= \int_{-\tau w/2}^{\tau w/2} s(t - \tau, Elm) \cdot hdet(\tau) \cdot d\tau$$

D(t, Elm) contains the detection-convolution results for each element 'Elm' at each time 't', wherein the detection-estimation process is integrating the undistorted signals s(t, Elm) over a certain detection-time span 'τw'. In this convolution, there is no receive delay involved, that changes nonlinear in time, during the integration over the time-span 'τw', therefore the I,Q-detection vectors D(t, Elm) are not afflicted with any form of distortion. The beamforming process can now use the I,Q-detection results available at the receive focus delay moments (t−τdel(t, Elm)), without being afflicted with an internal signal distortion generated by the beamforming process itself. The I,Q beamforming process, acting on the complex I,Q Rf signals produced by the I,Q-detection D(t, Elm), can be formalized as:

$$DBF(t) = \sum_{Elm} D(t - \tau del(t, Elm), Elm)$$

A time discrete version of this I,Q-beamforming, producing outputs at time discrete moments at t=k·Tout, can have (reduced) receive focus delay sets τdel(k·Tout, Elm) related to only these output moments.

$$DBFd(k) = \sum_{Elm} D(k \cdot Tout - \tau del(k \cdot Tout, Elm), Elm)$$

Formalization of the present invention delay and sum beamforming, with time discrete outputs, follows by substitution of the previous formulas, with as a result (3).

$$DBFd(k) = \quad (3)$$
$$\sum_{Elm} \int_{-\frac{\tau w}{2}}^{\frac{\tau w}{2}} s(k \cdot Tout - \tau - \tau del(k \cdot Tout - \tau, Elm), Elm) \cdot h(\tau) \cdot d\tau$$

The estimations of the I,Q-vectors (detection), D(k·Tout−τdel(k·Tout, Elm), Elm) is realized prior to the beamforming process, by integration over the detection time-window 'τw'. Therefore in (3) τdel(k·Tout−τ,Elm) can be a viewed as a fixed receive time-delay value at an output center τ=0, where this fixed delay value τdel(k·Tout, Elm) remains the same value, during the integration over the time-window from τ=(k·Tout−τw/2) . . . τ=(k·Tout+τw/2), as is expressed in FIG. 2d).

I,Q-Detection and Pre-Computed Interpolation Prior to the Multi-Line Beamforming Process.

The present invention demonstrates a receive focusing delay and sum beamforming utilizing a very high dynamic range and very low distortion. The conceptual aspects of the present invention is based on the equation (3), wherein the estimation of the I,Q-vectors (being I,Q-detection), is placed prior to the beamforming delay and sum stages, this will render the beamforming to be fundamentally distortion-less. In the equation (3), for simplicity, an infinite small time-delay delay resolution is assumed. In practice, interpolation on the digitalized receive signals, is mandatory, due to the practical limitations on the sample time of the digitalization of the received Rf-signals. Interpolation on the I,Q-vectors is to realize sufficient fine-delay-resolution, this relates to the dynamic range of the beamforming. A true fine delay of the signals is needed to prevent signal-distortion (to prevent different delay of the carrier and envelope of the signals), this must be performed by means of a true interpolation, wherein high performance interpolation is mandatory to prevent an additional signal distortion generated by interpolation stages itself. Straight forward up-sample interpolation, which is computationally more intensive for normal interpolation, is used because in the application of a multi-line beamforming, the interpolation results can be reused for each multi line, therefore the up-sample interpolation process actually pre-computes extra in between samples needed for the high resolution delay stages, wherein each multi-line beamforming can make use of the pre-computed interpolated I,Q-samples, the fact that each multi-line can use the pre-computed samples, makes it very computational efficient compared to the usage of a poly-phase interpolation scheme for each multi-line.

I,Q-Rf Beamforming.

Equation (3), shows the actual beamforming process is being performed after the convolution of the received signals with the hdet($\tau$) of complex (I,Q) nature. In the ultrasound beamforming process, high dynamic ranges are due to the coherent-summation, wherein, being at the spatial receive focus position, the signals from each element are in-phase, resulting in a high beamforming output amplitude, whereas being outside the spatial receive focus position, the signals from each element are not in-phase, resulting in a low beamforming output amplitude. The beamforming must keep the phases of the original received Rf-signals intact, meaning that it is mandatory to use the original Rf-signals, with the Rf-frequency equal to the transmitted Rf-frequency fc, at the delay and summing stages. Therefore the I,Q beamforming must use the I,Q-versions of the original Rf-signals, being I,Q Rf, and therefore the I,Q beamforming is named as I,Q Rf beamforming.

According to an embodiment of the present invention the method for performing a distortion free multi line receive focusing beamforming of ultrasound signals, comprises the steps of:

transmitting transmit beams from an array transducer comprising a certain number of transducer elements to a target;

receiving echo signals from at least part of the transducer elements of the array transducer;

obtaining receive signals from each of the said transducer elements of an array transducer;

complex detecting the receive signals from each transducer element to obtain complex detected signals having in-phase (I) and quadrature (Q) components;

carrying out the delay and sum beamforming of the complex detected signal components of each transducer element.

According to a further embodiment of the present invention, a method for performing a distortion free multi line receive focusing beamforming of ultrasound signals, comprises the steps of:

transmitting transmit beams from an array transducer comprising a certain number of transducer elements to a target;

receiving echo signals from at least part of the transducer elements of the array transducer;

obtaining receive signals from transducer elements of an ultrasound probe;

complex detecting the receive signals from transducer element, prior to a delay section, to obtain complex detected signals having in-phase (I) and quadrature (Q) components;

obtain, pre-computed, up sampled, interpolated, I,Q-Rf (in phase and quadrature Radiofrequency) signals with high-time-resolution;

applying time delay and decimation on the I,Q-Rf signals with high-time-resolution, to form delayed complex detected I,Q-Rf signals;

summing, in a coherent manner, the delayed complex detected I,Q-Rf signals to produce a dynamic focus receive beamforming output of complex detected I,Q-Rf output signals, and in which the step of obtaining pre-computed, up sampled, I,Q interpolated, I,Q-Rf, signals with high-time-resolution includes:

applying several complex interpolators in a cascade chain, wherein a depth dependent tracking filter (VCF) functionality might be included;

and when the complex detected signal is not on the fc frequency location, applying, a I,Q conversion to I,Q-Rf.

With the term I,Q-RF signals the in phase (I) and quadrature (Q) signal components at radiofrequency are indicated.

According to an embodiment complex detected I,Q signals are produced by a complex detection performed on the signals received by the probe, i.e. by the transducer array elements, for estimating I,Q vectors, and the method comprises the steps of converting the carried frequency of the I,Q detected receive signals to a predetermined working frequency (fx); generating I,Q detected receive signals with high time resolution by up sampling the complex detected I,Q detected signals by complex interpolation filters and converting the I,Q detected receive signals with high time resolution and with a working carrier frequency (fx) to I,Q-Radiofrequency receive signals with high time resolution, with the original ultrasound carrier frequency fc.

According to a variant embodiment, the working carrier frequency is set to 0 and the I,Q detected receive signal is converted to base bend I,Q complex signal by the complex detection and after the I,Q, base band receive signals is up sampled by complex interpolation filter to a I,Q detected receive signal with high time resolution the said signal is converted to a I,Q radiofrequency receive signals with high time resolution and with the original carrier frequency (fc).

According to an embodiment, the said complex detection is equivalent or comparable to a complex convolution on the signals received by the tranducer elements, with a resulting effective complex-impulse response hdet(t) according to the following equation:

$$D(t,\text{Elm})=s(t,\text{Elm})*h\text{det}(t)=\int_{-\tau w/2}^{\tau w/2} s(t-\tau,\text{Elm}) \cdot h\text{det}(\tau) \cdot d\tau$$

wherein the detection-estimation process consists in integrating the received signals s(t, Elm) by each transducer element (elm) over a detection-time span 'τw'.

According to an embodiment the time parameter 't' can be a time-continuous parameter or a time-discrete parameter with t=n·Tsam, the integral becoming a summation, acting on signal samples that are equidistant sampled.

According to further embodiment the said detection-time span 'τw', or the I,Q detection integration length, covers the impulse-length/bandwidth of the original Rf-signals received by the transducer elements.

A further embodiment provides that depending on the signals bandwidth a decimation on the I,Q detected signals is performed.

According to still another embodiment of the method the I,Q Rf detected signals with high-time-resolution, are obtained by means of pre-computed, up sampled, I,Q interpolation, using a plurality of complex interpolators in a cascade chain, to realize a higher time-delay resolution, with at least sixteen I,Q samples per fc-cycle.

According to an embodiment of the present method, the following steps are carried out prior to carry out the step of applying the beamforming delays and carrying out the coherent summation of the I,Q Rf receive signals of the transducer elements:
receiving Rf signals by each transducer element (elm);
converting the received RF signal to complex form (I,Q);
applying complex signal modulation for shifting the signal spectral content in frequency of the complex signals (I,Q) from the carrier frequency (fc) of the transmitted beam to a carrier working frequency (fx);
bandpass filtering the complex signal (I,Q) around the working carrier frequency (fx) for passing only the spectral content of the complex signal (I,Q) around the said working carrier frequency (fx);
shifting back the spectral content of the complex signal (I,Q) around the working carrier frequency (fx) to the original Rf carrier frequency of the transmit beam (fc);
generating higher amount of samples with a finer delay-resolution by a complex interpolation of the complex signal (I,Q) with the spectral content shifted back to the original Rf carrier frequency (fc) by complex interpolation filtering with a wideband passband filter;
providing high resolution delay samples of the complex signal (I,Q) with the spectral content shifted back to the original Rf carrier frequency (fc) each sample corresponding to finer delay-resolution than the initially sampled received signals before the step of conversion to a complex receive signal (I,Q);
choosing among the samples of complex signals (I,Q) the complex signal having the most appropriate high resolution delay.

According to a variant embodiment of the present method, the following steps are carried out prior to carry out the step of applying the beamforming delays and carrying out the coherent summation of the I,Q Rf receive signals of the transducer elements:
receiving Rf signals by each transducer element (elm);
converting the received RF signal to complex form (I,Q);
applying complex signal modulation for shifting the signal spectral content in frequency of the complex signals (I,Q) from the carrier frequency (fc) of the transmitted beam to a carrier working frequency (fx);
bandpass filtering the complex signal (I,Q) around the working carrier frequency (fx) for passing only the spectral content of the complex signal (I,Q) around the said working carrier frequency (fx);
generating higher amount of samples with a finer delay-resolution by a complex interpolation of the complex signal (I,Q) with the spectral content shifted at the working carrier frequency (fx) by complex interpolation filtering with a wideband passband filter;
shifting back the spectral content of the complex signal (I,Q) around the working carrier frequency (fx) to the original Rf carrier frequency of the transmit beam (fc);
providing high resolution delay samples of the complex signal (I,Q) with the spectral content shifted back to the original Rf carrier frequency (fc) each sample corresponding to finer delay-resolution than the initially sampled received signals before the step of conversion to a complex receive signal (I,Q);
choosing among the samples of complex signals (I,Q) the complex signal having the most appropriate high resolution delay.

According to a further variant embodiment the carrier frequency shift in the above two variant embodiments is set as the difference of the working carrier frequency and the original carrier frequency (fc) of the transmit beam, namely (fx−fc) and fx is chosen as 0, determining a carrier frequency shift (−fc) from the Rf original carrier frequency to the base band frequency and vice versa at the two shifting and back-shifting steps according to the two above variant embodiments.

According to an embodiment after the step of choosing the appropriate complex signal sample shifted back at the original carrier frequency and corresponding to a certain high resolution fine delay, to the said signal the corresponding beamforming delay and optionally the RTB delays and apodization weights are applied before coherent summation with the other samples complex signals (I,Q) determined from the Rf received signals of the other transducer elements.

According to still another embodiment of the method the step is provided of applying time delay and decimation on I,Q Rf signals with high-time-resolution, to form delayed complex detected I,Q Rf signals, wherein the time delays (τdel(k·Tout−τ,Elm)) to perform the receive focalization include the addition of multi-line transmit-delay corrections and the obtained delayed I,Q Rf signal are determined by selecting in a decimation manner, an appropriate I,Q Rf sample out of the, with high time resolution, available pre-computed I,Q Rf signal samples, in accordance with the time delay needed for the transducer element corresponding to the received I,Q-Rf signal.

According to still another embodiment of the method the step is provided of summing, in a coherent manner, the delayed complex detected I,Q Rf signals D(t, Elm), of the transducer elements (elm), with high time resolution, producing a dynamic focus receive beamforming output of complex detected I,Q Rf output signals. The beamforming being carried out according to the following equation:

$$DBFd(k) = \sum_{Elm} \int_{-\tau w/2}^{\tau w/2} s(k \cdot Tout - \tau - \tau del(k \cdot Tout - \tau, Elm), Elm) \cdot h(\tau) \cdot d\tau \quad (3)$$

and whereby, during the integration over the I,Q detection time-window, $\tau=(k-Tout-\tau w/2) \ldots \tau=(k-Tout+\tau w/2)$, the delay value τdel(k·Tout, Elm), remained a constant value.

According to a further embodiment the method according to one or more of the preceding embodiments is provided in combination with a retrospective dynamic transmit focusing beamforming technique. Different variants of this technique are known which are disclosed for example in document U.S. Pat. No. 8,137,272. In this document, a method for producing an ultrasound image with an extended focal range which can be provided in combination with the method for beamforming described above comprises the steps of:

> transmitting a plurality of transmit beams from an array transducer, each transmit beam being centered at a different position along the array and each transmit beam encompassing a plurality of laterally spaced line positions which are spatially related to laterally spaced line positions of another beam;
> receiving echo signals with the array transducer;
> concurrently processing the echo signals received in response to one transmit beam to produce a plurality of receive lines of echo signals at the laterally spaced line positions of the beam;
> repeating the concurrently processing for additional transmit beams;
> equalizing the phase shift variance among receive lines at a common line position resulting from transmit beams of different transmit beam positions;
> combining echo signals of receive lines from different transmit beams which are spatially related to a common line position to produce image data; and producing an image using the image data.

According to this solution the array transducer elements are connected to a multiline receive beamformer which produces a plurality of receive lines at a plurality of corresponding line positions in response to one transmit beam at each one of a certain number of different beam locations. The multiline receive beamformer operates by using the traditional beamforming technique, namely the so called delay and sum in which the delays are determined by the relative position of the focal point of the transmit beam, the points on the receive line and the transducer position in the array. According to the present invention prior of applying the delay and sum beamforming the step of one or more of the embodiments of the method disclosed above may be carried out. Furthermore, the delays may be determined for all the multiline beamformers along each receiving line according to the fine delay determination of the one or more variant embodiments described above.

According to a variant embodiment of the method, one or more of the embodiments of the method described above, may be combined with a method for performing retrospective dynamic transmit focusing beamforming for ultrasound signals comprising the steps of:

> a) transmitting a plurality of transmit beams from an array transducer, each transmit beam being centered at a different position along the array and each transmit beam having a width or an aperture encompassing a plurality of laterally spaced line positions, each transmit beam width or aperture overlapping at least partially at least the width or the aperture of the immediately adjacent transmit beam or of more laterally spaced transmit beams;
> b) receiving echo signals with the array transducer;
> c) processing the echo signals received in response to one transmit beam to produce a plurality of receive lines of echo signals at the laterally spaced line positions within the width or the aperture of the transmit beam;
> d) repeating the receiving step b) and the processing step c) for the additional transmit beams of the plurality of transmitted transmit beams of step a);
> e) equalizing the phase shift variance among receive lines at a common line position resulting from transmit beams of different transmit beam positions;
> f) combining echo signals of receive lines from different transmit beams which are spatially related to a common line position to produce image data; and
> g) producing an image using the image data;
> and in which the step e) of equalizing the phase shift is carried out concurrently with in the processing step c) and d);
> and in which the steps c) to e) are carried out on pre-computed, up sampled, I,Q interpolated, I,Q Rf, signals with high-time-resolution after the steps of:
> complex detecting the receive signals from transducer element, prior to a delay section, to obtain complex detected signals having in-phase (I) and quadrature (Q) components;
> obtain, pre-computed, up sampled, interpolated, I,Q-Rf (in phase and quadrature Radiofrequency) signals with high-time-resolution by
> applying several complex interpolators in a cascade chain, wherein a depth dependent tracking filter (VCF) functionality might be included;
> and, when the complex detected signal is not on the fc frequency location, applying, a I,Q conversion to I,Q Rf.

According to still another embodiment for each transmission of a transmit beam with a certain aperture, the received echoes are processed by a set of beamformer processors, each one related to a different line of sight;

each beamformer being characterized by a set of dynamic delays and optionally by a set of apodization weights, which are different for each beamformer processor and which dynamic delays are given by the sum of focalization delays and RTB delays, which are the phase shifts between the wave fronts of the different transmit beams centered at different transmission lines at the focal points along one receive line having a certain line location.

The present invention relates also to an ultrasound system, comprising:

an ultrasound probe including an array of transducer elements transforming electric input signals in acoustic transmit signals and transforming acoustic echo signals in electric receive signals;

a transmit beamformer generating the driving input signals for the transducer elements according to a transmit scheme for driving the transducer array to transmit a plurality of transmit beams from an array transducer;

the transmit beamformer including a memory configured to store time delays to synchronize contributions of transmit signals of the transducer elements of the array according to the said transmission scheme;

a receive beamformer including a receive signals processing unit configured to process the echo signals received in response to the transmit beams to produce a plurality of receive lines of echo signals;

a focalization delay module which applies to each receive signal contribution of each channel or transducer element the corresponding focalization delay for re-aligning the time of arrival of the receive signal contributions at the transducer elements of the transducer array from each reflecting or focus point;

an image generation unit producing an image producing using the said line image data.

a complex demodulator, with bandwidth limiting filters, and with a decimation capability, as complex detection of the receive signals from each transducer element to generate I,Q detected complex receive signals;

an up sampling complex interpolation filter unit of each I,Q detected complex receive signals, to generate I,Q detected receive signals with high time resolution;

a memory to store receive focus time delays in connection with a plurality of receive elements;

the said a complex demodulator, the said up sampling complex interpolation filters and the said memory being provided between an input of the Rf receive signals of each transducer element and the input of the focalization module;

the focalization module further comprising an I,Q Rf delay buffer, to temporary hold the I,Q Rf receive signals with high time resolution, to apply time delays to form delayed I,Q Rf receive signals and sum, in a coherent manner, the delayed I,Q Rf signals to obtain focused receive I,Q Rf beamformer output.

According to a further embodiment of the said ultrasound system comprises a multiline beamformer and particularly a retrospective dynamic transmit focusing beamformer, the said multiline beamformers comprising a multiline processor for each receive line encompassed by the aperture or the width of each transmit beam centered on a certain transmit line position.

An embodiment of the said ultrasound system comprises:
a transmit beamformer generating the driving input signals for the transducer elements according to a transmit scheme for driving the transducer array to transmit a plurality of transmit beams from an array transducer, each transmit beam being centered at a different position along the array and each transmit beam having a width or an aperture encompassing a plurality of laterally spaced line positions, each transmit beam width or aperture overlapping at least partially at least the width or the aperture of the immediately adjacent transmit beam or of more laterally spaced transmit beams;

the transmit beamformer including a memory configured to store time delays to synchronize contributions of transmit signals of the transducer elements of the array according to the said transmission scheme;

a receive beamformer including a receive signals processing unit configured to process the echo signals received in response to one transmit beam to produce a plurality of receive lines of echo signals at the laterally spaced line positions within the width or the aperture of each of the transmit beams of the said plurality of transmit beams;

a focalization delay and phase equalization delay module which applies to each receive signal contribution of each channel or transducer element the corresponding focalization and phase shift equalization delays for re-aligning the time of arrival of the receive signal contributions at the transducer elements of the transducer array from each reflecting or focus point and for equalizing the phase shift variance among receive line signals for each reflecting or focus point at a common line position the said receive line signals resulting from transmit beams of different transmit beam positions based on stored delay and phase shift values among receive lines at a common line;

a summer for summing for each receive line at each receive line position within the width or aperture of a transmit beam the re-aligned and phase shift equalized receive signal contributions of the transducer elements from focus points on the said receive line position after having applied to them the focalization delay and the phase shift equalization delay;

a memory connected to the receive beamformer and configured to store the said plurality of processed received lines of echo signals along a common receive line position resulting from transmit beams of different transmit beam positions;

a line combination module connected to the said memory and configured to combine echo signals of receive lines from different transmit beams which are spatially related to a common line position to produce line image data.

According to a further embodiment of the ultrasound system, the complex demodulator with bandwidth limiting filters operates as a carrier frequency converter or shifter of the spectral content of the complex receive signals (I,Q) at the carrier frequency of the transmit beam to a different carrier frequency (fx), a complex multiplier as a converter, to convert the I,Q detected receive signals with high time resolution, with a working carrier frequency (fx), to complex signals (I,Q-Rf) with high time resolution, with the original ultrasound carrier frequency fc, following the complex signal (I,Q) interpolation filter unit.

According to a further embodiment the I,Q Rf delay buffer readout, is configured to perform decimation on the I,Q Rf signals to be coherently summed, to produce an I,Q Rf beamformer output.

In an embodiment of the present ultrasound system, the complex signal (I,Q) interpolation filter unit comprises a cascade of up sampling complex interpolation filters generating I,Q detected receive signal samples with high time resolution.

According to a variant embodiment, the cascade interpolation filter is a wide-band filter with a plurality of zero filter coefficients.

A further improvement of one or more of the preceding ultrasound system embodiments provides an interpolation filter unit, or a cascade interpolation chain with a depth dependent tracking filter (VCF) functionality, wherein the nonzero filter coefficients, become altered under a depth depending control by the said depth dependent tracking filter.

According to a further embodiment the decimation and up-sample factor is dependent on signal bandwidth, complex detection integration length and up-sample interpolation and decimation at the delay buffer read out of the complex receive signals (IQ-Rf) and the beamformer output sample rate per multi-line is determined as $$\frac{1}{M} \cdot \frac{2^{NrCascadeStages}}{N} \cdot Fsam$$

Where
M is a decimation factor at the complex receive signal detector, $$\frac{Fsam}{M}$$

is the sample rate of the complex receive signal (I,Q);

$$\frac{Fsam}{M} \cdot 2^{NrCascadeStages}$$

the sampling frequency of up-sample of the cascade interpolation filter unit;

N is a sampling frequency reducing facto at the read out of the complex receive signals (I,Q Rf) samples from the delay buffer.

According to a further improvement which can be provided in combination with any of the above embodiments of an ultrasound system according to the present invention, the beamforming module, particularly the multiline beamformer is provided with a unit applying an apodization weight to the receive signals prior to coherent summation.

According to a further embodiment the above ultrasound system and specifically the receive beamformer may be in the form of a hardware unit or of a generic processing unit, comprising one or more processors configured to execute a program which provides instructions to the processing unit and/or to peripherals thereof to operate according the combination of units of one or more of the preceding embodiments.

According to a variant embodiment the above ultrasound system in which instead of 1d time domain processing, also 1d frequency domain processing might be utilized.

The invention relates also to a beamforming processor for carrying out the method according to one or more of the preceding embodiments and variants of the said method, which beamforming processor comprises:

a receive signals processing unit configured to process the echo signals received in response to the transmit beams to produce a plurality of receive lines of echo signals;

a focalization delay module which applies to each receive signal contribution of each channel or transducer element the corresponding focalization delay for re-aligning the time of arrival of the receive signal contributions at the transducer elements of the transducer array from each reflecting or focus point;

an image generation unit producing an image producing using the said line image data.

a complex demodulator, with bandwidth limiting filters, and with a decimation capability, as complex detection of the receive signals from each transducer element to generate I,Q detected complex receive signals;

an up sampling complex interpolation filter unit of each I,Q detected complex receive signals, to generate I,Q detected receive signals with high time resolution;

a memory to store receive focus time delays in connection with a plurality of receive elements;

the said a complex demodulator, the said up sampling complex interpolation filters and the said memory being provided between an input of the Rf receive signals of each transducer element and the input of the focalization module;

the focalization module further comprising an I,Q Rf delay buffer, to temporary hold the I,Q Rf receive signals with high time resolution, to apply time delays to form delayed I,Q Rf receive signals and sum, in a coherent manner, the delayed I,Q Rf signals to obtain focused receive I,Q Rf beamformer output.

According to a further embodiment of the said beamformer is a multiline beamformer and particularly a retrospective dynamic transmit focusing beamformer, the said multiline beamformers comprising a multiline processor for each receive line encompassed by the aperture or the width of each transmit beam centered on a certain transmit line position.

The above beamformer may comprise one or more of the features disclosed in relation to the above embodiments of the ultrasound system.

Emerging ultrasound systems, motivates the search for novel detection of applications. The capability of application-detections, needs an ultrasound system to be capable of detecting the applications-features, very accurate and at high speed. Typically, prior-art dynamic receive focusing, delay and sum, beamformers are used in ultrasound beam formers, followed with various kind of detections, for various applications, that are positioned after a beam former output. As shown above, prior art dynamic receive focusing beam formers generate signal distortions, that are fundamentally internally generated by the dynamic receive focusing beamformer process itself. These distortions, typically compromises the ability of accurate detections after the dynamic receive focusing beamforming.

In order to well perceive the fundamental concept of the present invention even further than as described by equation (3), it is essential to have a look at the fundamental interaction of reflections into a body/object.

An ultrasound system transmits an ultrasound-pulse of a certain frequency fc, positioned inside the transducers bandwidth. This transmitted pulse can be seen as:

$$sTx(t)=Atx(t)\cdot Ctx(t) \text{ with } Ctx(t)=\cos(2\cdot\pi\cdot fc\cdot t+PhTx)$$

wherein

Atx(t) is a pulse with a certain time length (Could be a Gaussian pulse, rectangular pulse, coded pulse or other shaped pulse).
 the spectral signal bandwidth of Atx(t) is positioned around 0 Hz.

Ctx(t) is the carrier signal.

fc is the frequency of the carrier.

PhTx reflects the static-phase of the carrier signal at the tx-moment t=0 cos( ) is a carrier-signal that acts as a catalyst, to enable the capture of the objects content, but this carrier alone has no spatial detection capability.
 the carrier Ctx(t) has no signal bandwidth, but its frequencies are located at −fc and +fc.

sTx(t) this transmitted signal acts as a catalyst, that also has spatial detection capability.
 the spectral signal of sTx(t) has a bandwidth positioned around −fc and a bandwidth positioned around +fc.

During echo-detection mode Atx(t) typically is a pulse of short time length to enable high-spatial-resolution detection of reflections from structures in the object. During Doppler-Detection mode Atx(t) typically is a pulse of longer time length (burst) to enable detection with high SNR to capture low level reflections from typically red-blood cells. During coded-detection modes Atx(t) typically is a coded-pulse of some sort, to enable better detection of several features. Either way, it is the structures in the object that modulate the sTx(t) carrier-signal-pulse. It is to say the received signal is a summation of all the reflection on boundaries at different depth in the object, that causes the objects content to be transferred from the catalyst sTx(t) onto the received sRx (elm,t) signals. The received signals can be seen as:

$$sRx(elm, t) = \sum_{Trefl} Aobject(elm, t - Trefl) \cdot sTx(t - Trefl)$$

wherein

Trefl=2·Lrefl/C reflects the exact depth position (given the assumption of constant speed of sound 'C')

Aobject(elm, t−Trefl) relates to the strength of a reflection from an object (boundary density difference)

A simplified version of sRx(elm,t) will be used for further explanation. A typically received ultrasound Rf-signal, received on only one transducer element, has the form of an Rf-carrier (the transmitted pulse), modulated with information content of the object:

$$sRxelm(t) = A(t) \cdot \cos(2 \cdot \pi \cdot fc \cdot t + Ph(t))$$

wherein
sRxlm(t) reflects a ultrasound signal, received on only one element
A(t) Amplitude information (related to the object reflection strengths)
Ph(t) phase information (related to the object reflections positions)

The transmitted sTx(t) signal propagates through the body, during its travel it hits a target in the body, a portion of this signal energy is reflected and travels back towards the probes elements. After some time 'Trefl', a signal sRx(elm,t) is received on an element 'elm'. The form of sRx(elm, t) has a similar form as sTx(t) but 'Trefl' later in time, this situation can be reflected in the formula:

$$sRxelm(t) = A(t - Trefl) \cdot \cos(2 \cdot \pi \cdot fc \cdot (t - Trefl) + Ph(t - Trefl))$$

A distortion free detection of the signal sRxelm(t), received at an element 'elm', is to find a good estimate of the value AO at the moment t=Trefl. A( ) is strongly related to Aobject( ), so a good estimate of AO delivers a good undistorted detection/estimation of the objects content Aobject( ). The signal at the moment t-Trefl has the form:

$$sRelm(Trefl) = A(Trefl - Trefl) \cdot \cos(2 \cdot \pi \cdot fc \cdot (Tref - Trefl) + Ph(Trefl - Trefl))$$

$$sRxelm(Trefl) = A(0) \cdot \cos(Ph(0))$$

This shows that with sRxelm(Trefl), the detection of A(0) can only be found by the elimination of the cos(Ph(0)) term, this needs at least an integration/filtering over a length of at least one carrier-cycle around t-Trefl. This implies that detection of A(0), can only be realized by using the signal surrounding t=Trefl. In the case of a traditional dynamic receive focusing beamforming, the correct I,Q detection of A(0) is very complicated due to the changing delays of the dynamic receive focusing beam former, that produces signal surrounding t=Trefl that are non-equidistant sampled, which results in distorted signals around t=Trefl (FIG. 2a,b). As in the case of the I,Q Rf beamforming of the present invention, the I,Q detection is performed prior to the beamforming changing delay, a correct I,Q detection on original equidistant sampled Rf-signals is ensured, wherein the I,Q detection matches with the time-of-flight situation of the original on the elements received Rf-signals (FIG. 2c).

BRIEF DESCRIPTION OF THE DRAWINGS

Further features and advantages of the invention shall be described by means of detailed descriptions of embodiments of the present invention with reference to the Figures, wherein

FIG. 4c shows a schematic illustration of an example embodiment of signal processing blocks to realize the I,Q-detection and I,Q interpolation steps, prior to be used in the I,Q Rf beamforming. Wherein the I,Q detection, might consists of an Adc, a Rf to complex modulator, and poly-phase-low-pass filters, followed by a complex to complex modulator, and as an example three cascade interpolation stages, with a VCF option in front, wherein the interpolation is performed around an I,Q Rf-signal, prior to the high resolution delay stage.

FIG. 4e shows a schematic illustration of a detail of the diagram of FIG. 4c, to show that the cascade stages might be bypassed by means of multiplexers.

FIG. 4d shows a schematic illustration of an example embodiment of signal processing blocks to realize the I,Q-detection and I,Q interpolation steps, prior to be used in the I,Q Rf beamforming wherein the I,Q detection, might consists of an Adc, and poly-phase-low-pass filters, and as an example three cascade interpolation stages, with a VCF option in front, wherein the interpolation is performed around fx=0, followed by a complex to complex modulator, prior to the high resolution delay stage.

DETAILED DESCRIPTION OF VARIOUS EMBODIMENTS OF THE INVENTION

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Figure 1:
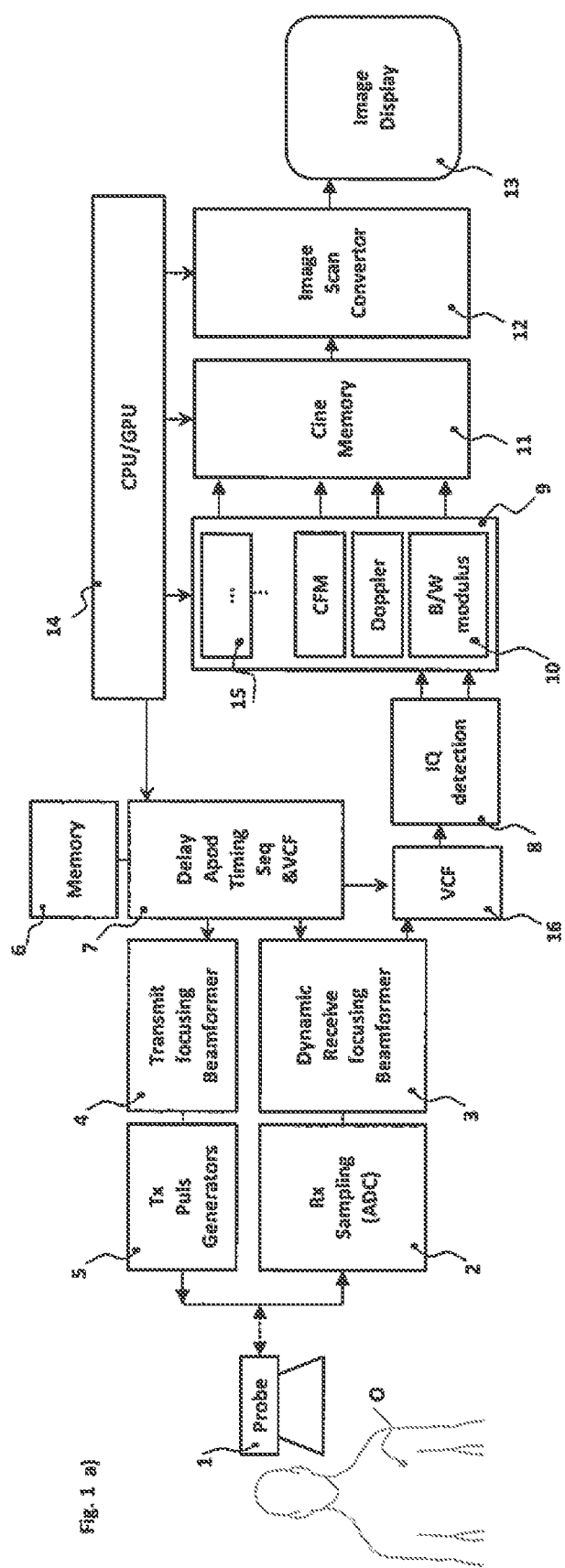
FIG. 1a shows 1a block diagram of an embodiment of an ultrasound system.
FIG. 1b shows a block diagram of a possible embodiment of a traditional, prior art, dynamic receive focusing beam former.
FIG. 1c shows a block diagram of an exemplary embodiment of the present inventions dynamic receive focusing beamforming that, fundamentally, has no internal distortion-generation.
Figure 1:
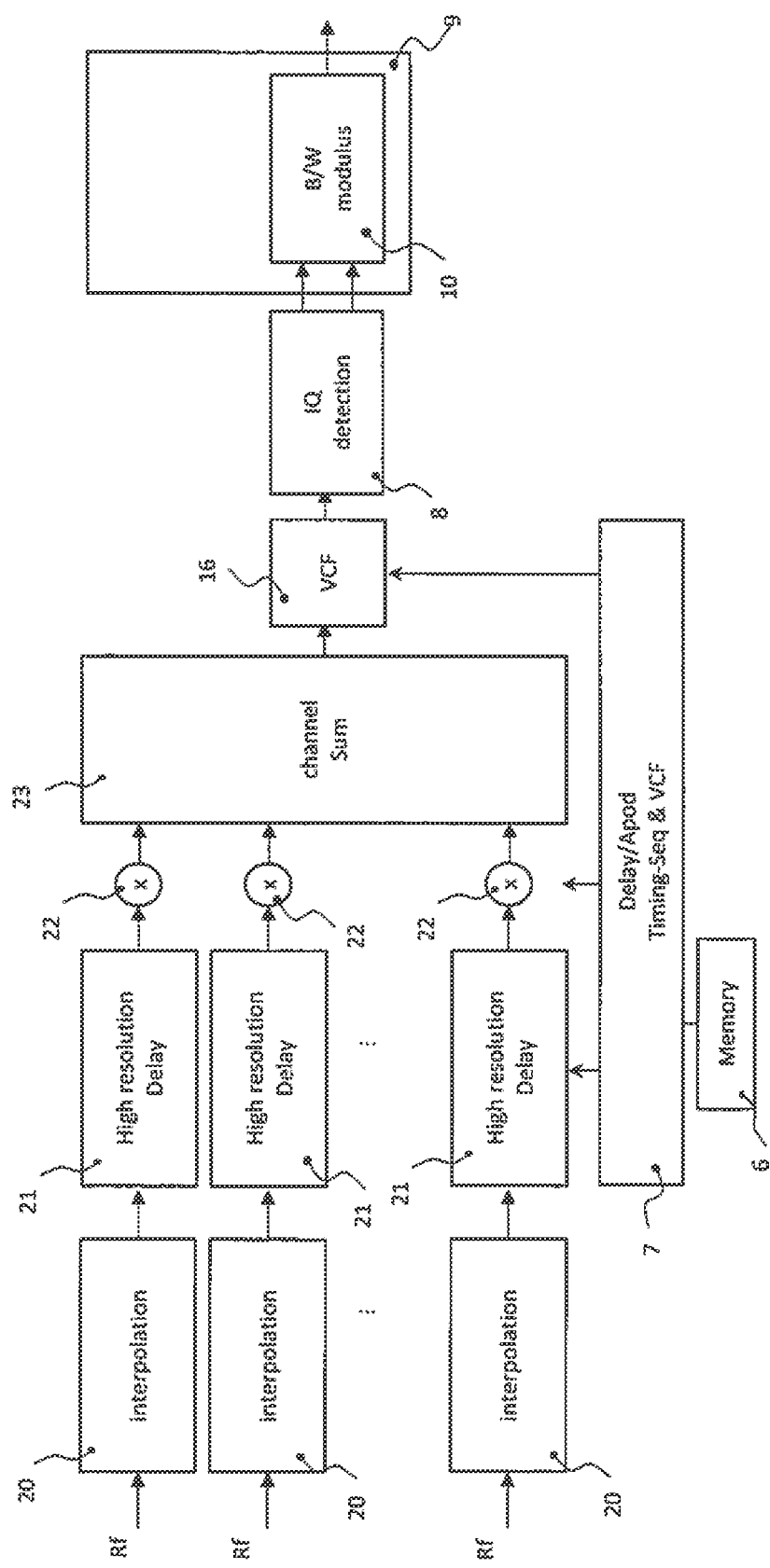

FIG. 1a shows an embodiment of an ultrasound system comprising the steps of: generation of transmit Rf-pulses by generator S with time profile information present in memory 6 being passed to a transmit focusing beam former 4 with a timing trigger control 7 creating a transmit beam profile being transmitted by means of an ultrasound probe 1 into an object O. Ultrasound waves travel through the object O, which will generate reflections related to the content of the object O. The reflections are received as Rf-signals on the elements elm of the probe 1. The received reflected Rf-signals are adequately sampled 2 and become processed by a dynamic Rf-based receive focusing beam former 3. The dynamic receive focusing beam profile information is present in memory 6 and is passed to the dynamic delay and apodization generators 7 to be used during the reception of Rf-signals to perform a dynamic receive focusing beamforming functionality 3. The beamformers Rf-signal output, might be processed by a depth dependent tracking filter 16 (VCF), and the processing continues with a I,Q-detector 8 that extracts an estimate of the objects content O, captured in I,Q-samples. Depending on the active modality the I,Q-samples will be processed in a feature-detector 9 that is fed to the active modalities specific feature-detection, as an example serves an envelope extraction 10 suitable for a B-mode modality. Well known feature-detections 9 are modalities specific-detectors as Doppler-mode, CFM-mode, or other novel modalities specific-detectors 15 might be used. The several extracted modality features might be temporarily stored in a cine-memory II to be further processed by a scan-converter 12 to convert the modality feature signals into a suitable image display format, to be displayed on an image-display 13. The ultrasound embodiment might be using a processor CPU/GPU 14 to provide a user interface to control several systems-modalities, and the CPU/GPU 14 might be used to perform several signal processing tasks 9, 11, 12.

An ultrasound dynamic receive focusing beam former 3 is illustrated in FIG. 1b. FIG. 1b shows as an example, a traditional Rf dynamic receive focusing delay and sum beamformer, with at the beamformer output a depth dependent tracking filter 16 (VCF), a detector 8 and envelope estimator 10 to perform, as an example, a B-mode modality feature-detection. The Rf-signals provided by the sampling stages (ADC) 2 are presented to the Rf-interpolation stages 20, that produces extra in between samples needed for the high resolution delay stages 21 to be able to select, during a decimate step, samples at a finer delay time resolution. This selection of samples relates to the receiver focusing profiles, of which the profile information is stored in memory 6 and converted in the actual controlling realized by the delay, apodization, timing stage 7. The beamforming process is completed with apodization multipliers 22 followed with coherent channel addition 23, which output becomes passed to a depth dependent tracking filter 16 (VCF), a I,Q-detector 8 and a modulus 10 to deliver this beam formers B-mode feature-detection result.

Figure 2A:
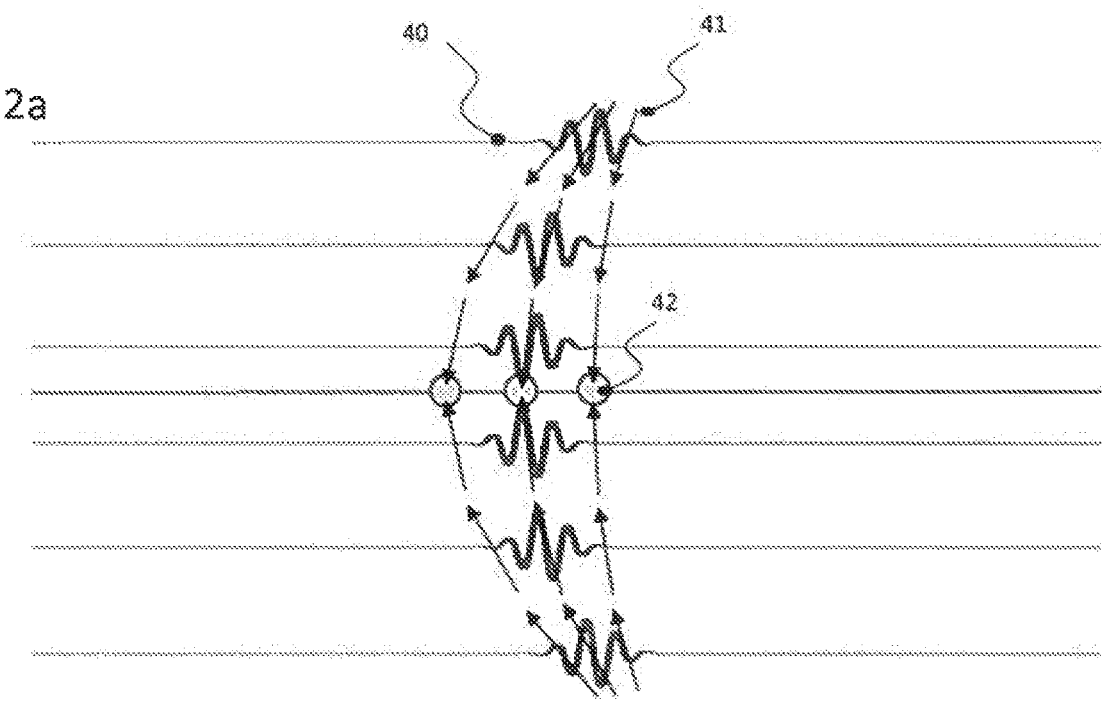
FIG. 2a shows a schematic illustration of, as an example, 6 received Rx(elm,t) time continuous signals that become sampled at time positions related to the ideal sample time moments of a dynamic receive focusing position.
Figure 2B:
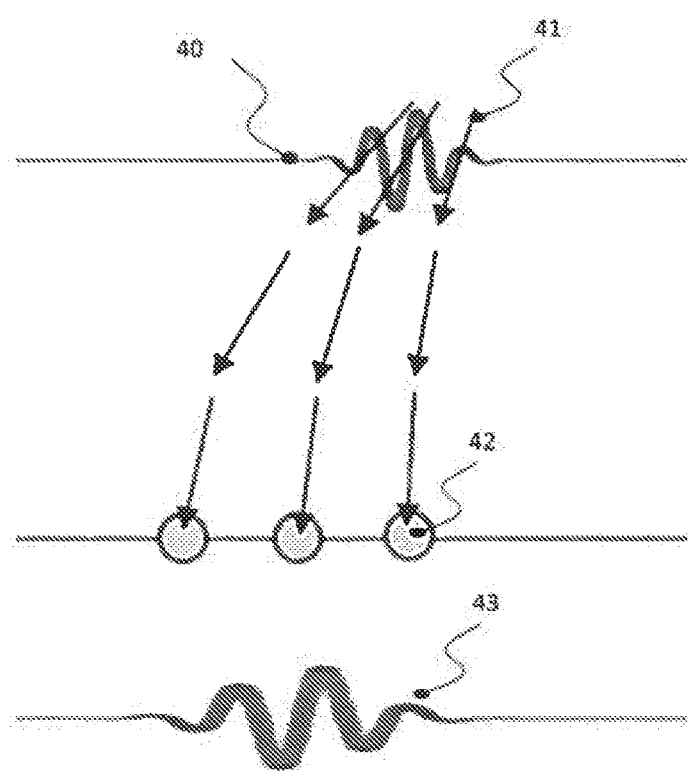
FIG. 2b shows a schematic illustration that explains the internal signal distortions that are a result of the changing sample positions which are an intrinsic part of a prior art dynamic receive focusing beamforming signal processing principle and consisting in non-equidistant sampling results, causing the internal signal distortions.

The traditional beam former of FIG. 1b suffers the fundamental problem of internal generation of signal distortion as more precisely demonstrated by the equation (2). FIG. 2a shows, the signals Rx(elm,t) received on each of the elements elm, that have, as an example, an undistorted time continuous signal shape like 40. This time continuous signal becomes sampled at time positions related to the ideal (infinite accurate delay-quantization) sampled time moments of the dynamic receive focusing position. The arrows 41 show how the samples of a dynamic receive focusing position, become projected during the beam former summation stage 23 onto the beam formers output samples 42 (these output samples are time equidistant). As is depicted in a detailed part FIG. 2b, it can be seen that the signal 40, results in a signal 43 which is present, as a part, in the beamforming output. The signal 43 is a nonlinear stretched signal version of the undistorted input signal 40, therefore the signal 43 is inflicted with internal signal distortions that is the result of the prior-art means of dynamic receive focusing signal processing. Even with infinite accurate delay-quantization, this signal distortion will be present in the outputs of prior-art beam formers. The fundamental problem lies in the fact that the prior art beamformers perform I,Q-detection 8 after the beam formers coherent summing 23. The I,Q-detector sees at its input the equidistant output samples of the prior art beam former output. But as described above, the distorted signal parts 43 are already present in the prior art beam formers equidistant output samples.

Figure 2C:
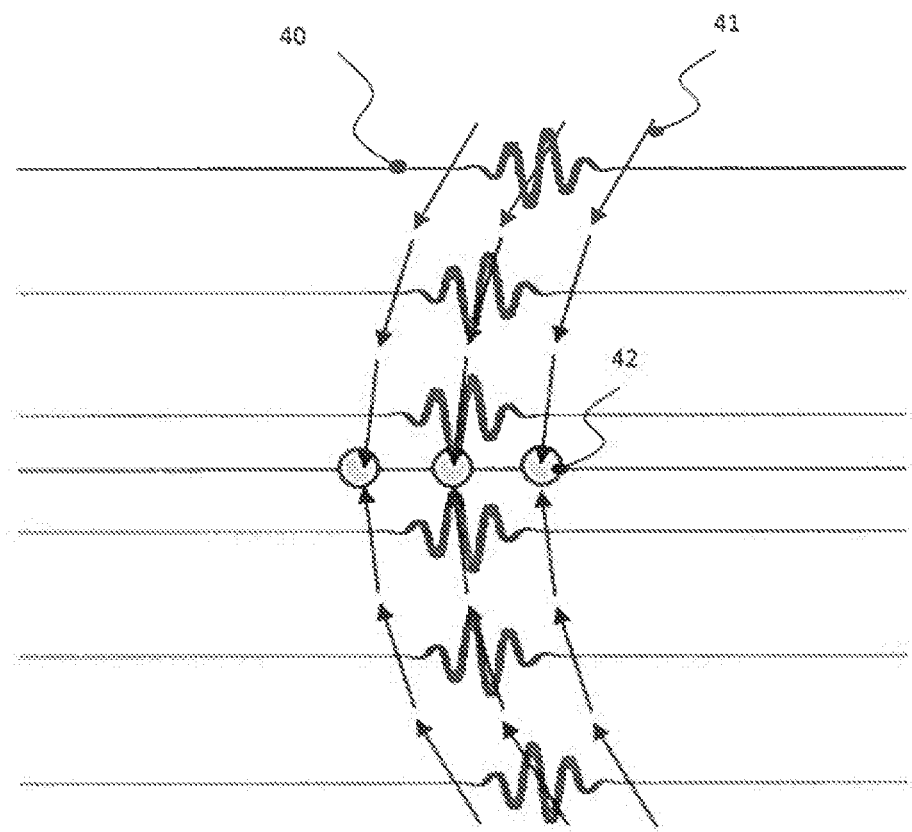
FIG. 2c shows a schematic illustration of the present inventions dynamic receive focusing I,Q-Rf beamforming, with the underlying principle of direct I,Q detection, where equidistant samples are used, and therefore the way of signal processing of the present invention, does not suffer any internal signal distortion.
Figure 2D:
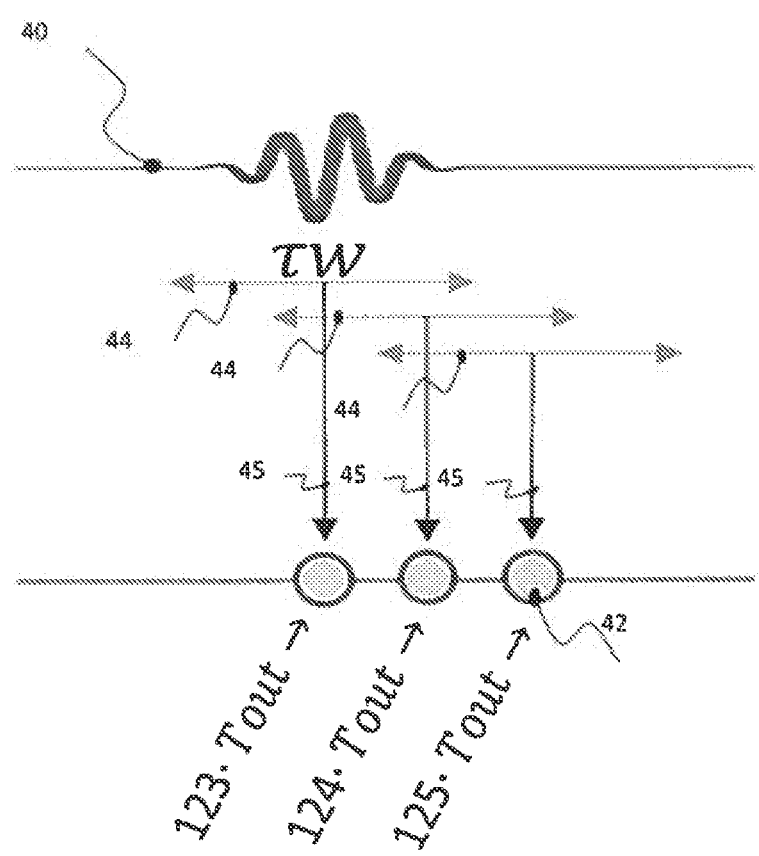
FIG. 2d shows a detail of the I,Q-detections integration, that is performed to produce time-discrete beamforming I,Q Rf output samples.

The beamforming of present invention FIG. 1c resolves the problem of internal generation of signal distortion. The received signals Rx(elm,t) as shown in FIGS. 2c and 2d, have, as an example, an undistorted time continuous signal shape like the one of FIG. 2c indicated by 40, which become equidistant sampled at 2 and become presented to an I,Q-detection at detector 8. Since this is the first step acting on the received signals Rx(elm,t), it will capture the signal shapes 40 in an undistorted manner, during the convolution/integration over τw of FIG. 2d as indicated by 44 as part of the I,Q-detection 8 process, concentrating the convolution/integration result in a I,Q vector sample as a good estimation of A(0).

Typically a I,Q detection stage 8 is a complex filter like a Hilbert-filter, this type of filter suppresses the negative frequency of the spectral content of a real ultrasound Rf-signal, coming from the sampling stages (ADC) 2, which results in a I,Q Rf-signal at its output. The spectral content of the I,Q Rf shows its signal power around the transmitter S transmitted frequency 'fc', therefore it will be named I,Q Rf. The I,Q-detector can produce good distortionless I,Q Rf samples out of the undistorted equidistant sampled input samples. Since the detection is already performed and captured in the distortion less I,Q Rf samples, in an early stage, the time shifting of the dynamic receive focusing beam former of the present invention has no influence on the beamformers output signal, because after the beamformers output the I,Q Rf samples directly become processed in a feature detector 9,10.

The exemplary embodiment of the present invention in FIG. 1c) shows a I,Q Rf dynamic receive focusing delay and sum beam former, with RTB capability, that demonstrates a very high dynamic range and a very low distortion, dynamic receive focusing beamforming quality.

In this embodiment after the detection step of the I,Q signals, the sampling of the I,Q signals and the interpolation of the I,Q signals in order to determine high resolution delays, a so called RTB delay component and an apodization component is added.

According to an embodiment, this RTB delay component corresponds to the phase shifts between the wave fronts of the different transmit beams centered at different transmission lines at the focal points along one receive line having a certain line location in combination with a multiline beamforming technique according to which following the transmission of a plurality of transmit beams from an array transducer, each transmit beam being centered at a different position along the array and each transmit beam encompassing a plurality of laterally spaced line positions which are spatially related to laterally spaced line positions of another beam, the received echo signals by the array transducer in response to one transmit beam are concurrently processed to produce a plurality of receive lines of echo signals at the laterally spaced line positions covered by the transmit beam. This concurrently processing is repeated for additional transmit beams and the phase shift variance among receive lines at a common line position resulting from transmit beams of different transmit beam positions are equalized. The echo signals of receive lines from different transmit beams which are spatially related to a common line position tare combined to produce image data which is used to produce an image.

The conceptual aspects of the present invention, are described in detail by equation (3) and cosists in placing the I,Q-detector 8 prior to the delay stages 31, this will render the beamforming to be fundamentally distortion less. According to this arrangement, the amount of dynamic range and the distortion that a practical beam former will reach, now only depends on the number of interpolated in between I,Q samples (delay quantization which relates to dynamic-range), and the quality of the interpolation (interpolation errors which relates to a remaining distortion level).

According to the present invention, the beam former uses complex signal processing, as it starts with an I,Q detection stage 8. The I,Q Rf-signals are used by the I,Q Rf interpolation stages 30, with a (optional) VCF functionality 82. Wherein 30 is a complex interpolation filter, with a good quality of interpolation, as is needed to realize a beam former with high dynamic range, low distortion and very accurate focusing selection.

The interpolation produces extra in between samples needed for the high resolution delay stages 31 to be able to select, during a decimate step, samples at a finer delay time resolution. This selection of I,Q Rf samples relates to the receive and RTB focusing profiles, of which the profile information is stored in memory 6 and converted in the actual controlling realized by the Rx+RTB delay, and apodization, timing stage 7. The beam form process is completed with apodization/aperture multipliers 32 that can weigh the I,Q Rf-signals. After that a coherent I,Q Rf channel addition 33 is performed, of which the I,Q Rf output becomes passed to a modulus 10 directly, to deliver this beam formers B-mode feature-detection result, this is possible because the whole beam former is realized in I,Q Rf.

Figure 3A:
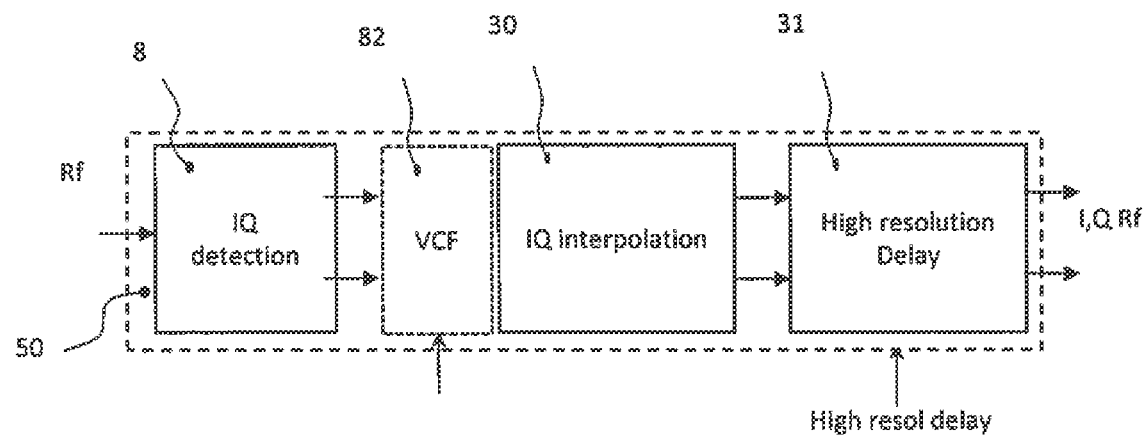
FIG. 3a shows a detail of the signal processing chain 50 of FIG. 1c for one channel, to reference alternative ways of processing with equal functionality.
Figure 3B:
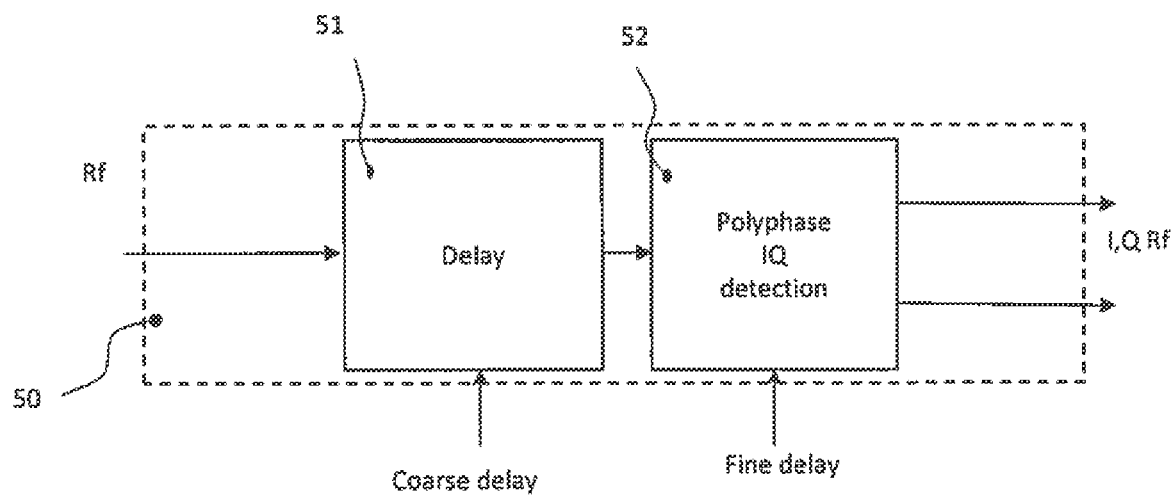
FIG. 3b shows a schematic illustration of a delay-memory to provide coarse delaying of Rf-samples, followed by a poly phase version of an I,Q-detection filter, that also provides a fine delay interpolation.

A further exemplary embodiment of the present invention is illustrated in FIG. 3a. FIG. 3a shows the signal processing chain 50 of one of the identical channels Ch1, Ch2, ChN, of the beam former of FIG. 1c. The I,Q-detectors 8 functionality is not only to convert the incoming Rf-signal 2 to a complex form, but also to function as the active filter, that has a complex impulse response length, that matches with the signal content bandwidth of sRxelm( ) positioned around fc, in order to realize a good estimation of A(0), and it improves the SNR. The I,Q-detector band limiting filter will need a lot of complex-filter coefficients, and the complex filter coefficients, need to change, dependent of the signals content of sRxelm( ), bandwidth and fc position. The I,Q interpolation filter 30 is a complex filter which produces in between complex I,Q Rf-samples, by means of up sampling. The amount of output samples is a factor 'IpolFac' higher than the amount of input samples. The higher amount of samples provide the availability of samples with a finer delay-resolution in the high resolution delay block 31, depending on the control 'high resolution delay', related to the needed receive and RTB beam form profile, I,Q-rf samples are picked out/decimated to produce with a certain sample rate the beam formers output samples illustrated by way of an example in FIG. 2c, indicated with 42. FIG. 3b) shows the same functionality as 50, the Rf-data becomes delayed 51 under the control of 'coarse delay', and then the poly-phase I,Q-detector 52 can produce the same I,Q Rf output, with the control of 'fine delay'. A poly-phase I,Q-detector of this sort might be used, regardless the computational and memory access disadvantages. This type of filter needs to perform per output NrTaps complex multiplies, and needs to read NrTaps, complex numbers for the filter functionality.

Figure 3C:
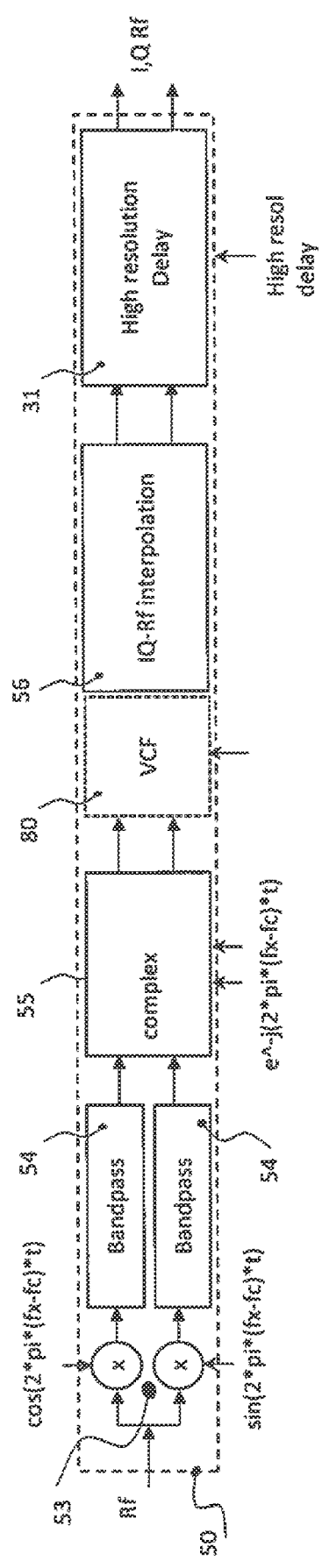
FIG. 3c shows a schematic illustration wherein the I,Q-detection is substituted by means of a Rf to complex modulator with complex bandpass filters, followed by a complex to complex modulator, and a I,Q Rf interpolation, with a VCF option in front, prior to the high resolution delay stage.

A third exemplary embodiment of the present invention is illustrated in FIG. 3c. FIG. 3c shows the signal processing chain 50 of one of the identical channels Ch1, Ch2, ChN, of the beam former of FIG. 1c. Here the I,Q-detection functionality becomes realized by means of, first a complex modulating stage 53 with an input Rf-signal sRxelm( ) coming from 2, that has its spectral signal content positioned around −fc and +fc:

$$sRxelm(t) = A(t) \cdot \cos(2 \cdot \pi \cdot fc \cdot t + Ph(t))$$
$$= A(t) \cdot \frac{(e^{j \cdot (2 \cdot \pi \cdot fc \cdot t + Ph(t))} + e^{-j \cdot (2 \cdot \pi \cdot fc \cdot t + Ph(t))})}{2}$$

The complex modulating stage 53 shifts the signal spectral content, in frequency over (fx−fc) this will result in spectral signal content around +fc+(fx−fc)=fx and −fc+(fx−fc)=fx−2·fc:

$$IQmfx(t) = A(t) \cdot \frac{(e^{j \cdot (2 \cdot \pi \cdot fc \cdot t + Ph(t))} + e^{-j \cdot (2 \cdot \pi \cdot fc \cdot t + Ph(t))})}{2} \cdot e^{j \cdot (2 \cdot \pi \cdot (fx-fc)t)}$$
$$= \frac{A(t)}{2} \cdot e^{j \cdot (2 \cdot \pi \cdot fx \cdot t + Ph(t))} + \frac{A(t)}{2} \cdot e^{-j \cdot (2 \cdot \pi \cdot (2 \cdot fc - fx) \cdot t + Ph(t))}$$

The bandpass filters 54, with the filters pass-band positioned around fx, will only pass the signals with the spectral content around fx, resulting a complex I,Q signal with its signal content around fx, therefore it will be named I,Q Rx. As can be seen, the I,Q Rx has the same signal content A(t), and Ph(t) as is present in sRxelm(t), only the carrier is different $$IQrx(t) = \frac{A(t)}{2} \cdot e^{j \cdot (2 \cdot \pi \cdot fx \cdot t + Ph(t))}$$

The IQrx(t) becomes shifted back in frequency content by means of the complex multiplier 55 that shifts the signal spectral content, in frequency over −(fx−fc), therefore the output signal of 55 will have its signal content positioned around fx−(fx−fc)=fc, as a result this output is an I,Q Rf-signal with the spectral signal content around the original fc:

$$IQrf(t) = \frac{A(t)}{2} \cdot e^{j \cdot (2 \cdot \pi \cdot fc \cdot t + Ph(t))}$$

For the beam forming process it is essential that the I,Q Rf has its spectral content around the original carrier frequency fc, this ensures that after the delay stages 31 the phases of the I,Q-rf signals have the correct phases at the coherent summing stage 33.

The band-pass filters 54 function as the active filters, that have an impulse response length, that matches with the signal content sRxelm( ) bandwidth around fx, in order to realize a good estimation of A(0) and improve SNR. The band-pass filters will need a great number of filter coefficients, and the filter coefficients, need to change, dependent of the signals content sRxelm( ), bandwidth. The benefit of the shifting of the signal content from fc to fx at 53 before the filters 54, and then shift it back again from fx to fc at 55, is that the filters 54 are always positioned around fx, regardless of the used transmitted carrier frequency fc. In FIG. 3c the I,Q Rf interpolation stage 56 is a complex interpolation filter with a wideband passband. Because this filter is located after the active filters 54, that already performed a good SNR signal processing, it is sufficient for this interpolation filter to be designed as a wider-band filter (shorter impulse-response length), wherein additionally, the filter coefficients can be optimized in the sense that a lot of zero filter coefficients can be used. Because this filter is a wide-band filter it might be a filter with fixed coefficients, as long as the signal content around fc is lying inside the wide bandpass.

Figure 3D:
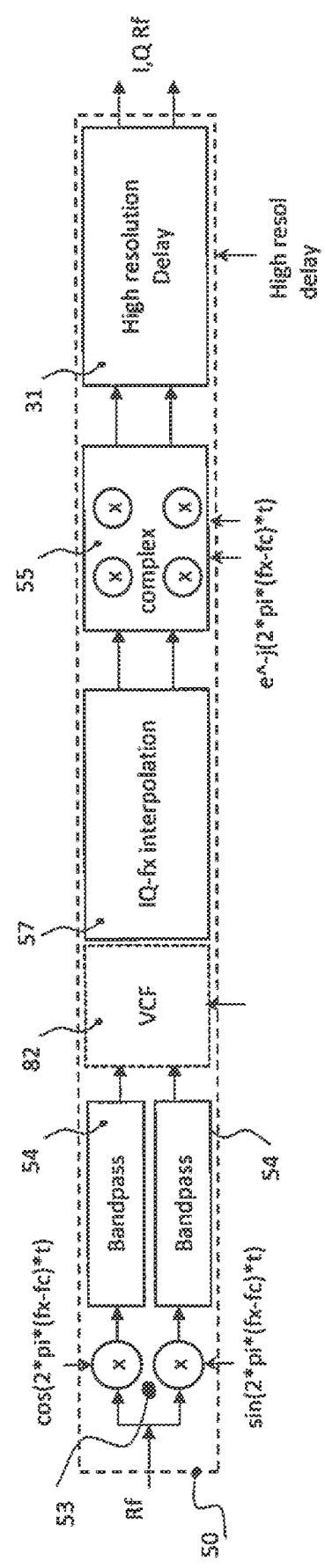
FIG. 3d shows a schematic illustration wherein the I,Q-detection is substituted by means of a Rf to complex modulator with complex bandpass filters, followed by IQ-fx interpolation, with a VCF option in front, followed by a complex to complex modulator, and a I,Q Rf interpolation prior to the high resolution delay stage.

FIG. 3d illustrates another embodiment, in which a complex interpolation filter 57 with a wideband passband around fx is used, because this filter is located after the active filters 54, that already performed a good SNR signal processing, it is sufficient for this interpolation filter to be designed as a wider-band filter (shorter impulse-response length), wherein additionally, the filter coefficients can be optimized in the sense that a lot of zero filter coefficients can be used. An additional benefit of positioning the interpolation filter 57 before the complex multiplyer 55 is that the spectral signal content is always positioned around the frequency fx, regards less the bandwidth of sRxelm( ), therefore the signal will always fit inside the bandpass of the filter 57.

Still a further embodiment of the present invention may be characterized by the following configuration: The embodiments of FIG. 3c) and FIG. 3d), uses frequency shifting of the spectral signal content, shifting the transmitted frequency fc to a fixed frequency fx, resulting in a spectral signal content positioned around the fixed frequency fx. Because in ultrasound the used transmitted frequencies fc are not always at a fixed frequency, having the signal content around a fixed frequency fx has the advantage of having the filters in FIG. 3d, indicated by 54, 57, pass-bands located around the fixed frequency fx. Modern ultrasound analogue front end devices (AFE) are already equipped with digital demodulators and digital low-pass filters with programmable filter coefficients, these devices provide the same functionality as the units 53, 54 where the shift over (fx−fc) is chosen to be (0−fc)=−fc. The resulting complex signal, named as I,Q-bb (where bb stands for Base Band), is the special case of I,Q Rx wherein fx=0:

$$IQbb(t) = \frac{A(t)}{2} \cdot e^{j \cdot (2 \cdot \pi \cdot 0 \cdot f + Ph(t))}$$
$$= \frac{A(t)}{2} \cdot e^{j \cdot (Ph(t))}$$

Another advantage of the embodiment according to FIG. 3d, is that the complex multiplier 55 in this case might also be used as a means of an additional interpolation, by producing additional (up-sample), in between complex I,Q Rf-samples, by means of a small additional rotation of the carrier. But care must be taken when using the small additional phase-rotation as it is not a fully correct way of delaying the signal, as can be easily seen, as the phase rotation only rotates the carrier vector, but does not delay the signals content A(t), this implies that the signal becomes distorted by some amount. But nevertheless it might be used as an additional interpolation step after the I,Q Rx interpolation 57. In U.S. Pat. No. 6,029,116 a conversion from I,Q-bb to I,Q Rf is used.

According to an improvement of U.S. Pat. No. 6,029,116 which discloses a base band beamforming techniques known in the state of the art, a base band beamforming method is disclosed comprising the steps of:

obtaining receive signals from transducers of an ultrasound probe;

demodulating the receive signals to obtain complex receive signals having in-phase (I) and quadrature (Q) components;

applying time delay and phase correction to the complex receive signals to form delayed complex receive signals, the time delay configured to align contributions of reflection signals received by the transducers of the array, the phase correction configured to correct phase differences; and summing, in a coherent manner, the delayed complex receive signals to produce a coherent receive signal focused at a reflection point or a reflection target. In a specific variant embodiment applying the phase correction includes: applying coarse and fine corrections, where the coarse correction calculated as a multiple of a sampling time; and the fine correction calculated as a fraction of the sampling time, and wherein the coarse and fine corrections are contemporaneously applied by multiplying the complex receive signal by a complex carrier delayed by a multiple of the sampling time and delayed by the fraction of the sampling time.

In this embodiment, a conversion from I,Q-bb to I,Q Rf is used at the delay-read-out, that includes an additional fractional phase rotation to perform a part of the total interpolation, the additional phase-rotation interpolation is done after the coarse-delay, so it can be seen as a partial interpolation in a poly-phase way, in multi-beam beamforming this solution, will need separate phase rotation control for each multi-line beamforming output.

For a practical beamformer of the present invention, it is mandatory to realize the filters in a very cost effective way, not only because the I,Q-detecting filters 8 and the interpolating filters 30 need to be located in front of the delay-sections 31, whereof NrChannel time filters are needed, but also because the I,Q detection and the I,Q interpolation needs to be performed with high quality, in order to create a beam former with very low distortion and high dynamic range.

According to an embodiment of the present invention, modern ultrasound analogue front end devices (AFE) might be used for the actively band limiting and I,Q-detection functionality. FIG. 4c and FIG. 4d show the usage of an AFE 60, which contains, a sampling stage (ADC) 2, complex demodulator 53 and low-pass filters 61, and decimation stages 62. During the conversion from Rf-signal to I,Q-bb (I,Q base band), the signals content around fc is shifted to signal content around fx=0, depending of the spectral signals bandwidth allows for a certain amount of decimation by a factor 'M' of the I,Q-bb signals. The poly phase low-pass filters 61 can have longer impulse response lengths for lower bandwidth signal. The signal processing in 60 is a good active filter with a good quality I,Q detection, with a good match of the signals bandwidth, and therefore a good means of SNR-signal processing. Therefore, the following interpolation stages can use wider band transfer functions, where filter coefficients with a lot of zero values are possible, to realize a very computational effective solution.

Realizing a high accurate focusing with a high dynamic range capability, needs a finer delay resolution as the sampling time of the ADCs 2 are capable of. The used delay resolution is directly related to how well the phase alignment in the beam formers coherent summing performs. A factor of two lower delay resolution time will result in 6 dB lower dynamic range. A good beamforming process uses at least 16 samples per fc cycle. The sampling of the ADC 2 might be to have about 4 samples per Rf-cycle in the case of a high frequency of fc. After the I,Q demodulation 53 and filters 61, the decimation step will have, when using a high frequency of fc, a value of M=2, so there will be about 2 I,Q samples per fc cycle available. This means that the I,Q interpolation filters should at least up sample by a factor of 8× (or more) in order the reach 16 samples, or more, per fc cycle. Delaying a signal with a good quality without altering the signals content, needs to be realized by means of interpolation. Interpolation ensures that the actual signal content can be fine-delayed, as interpolation enables a true delay. A good quality of interpolation is needed in order to have good distortion less coherent summing in the beam former process.

Figure 4A:
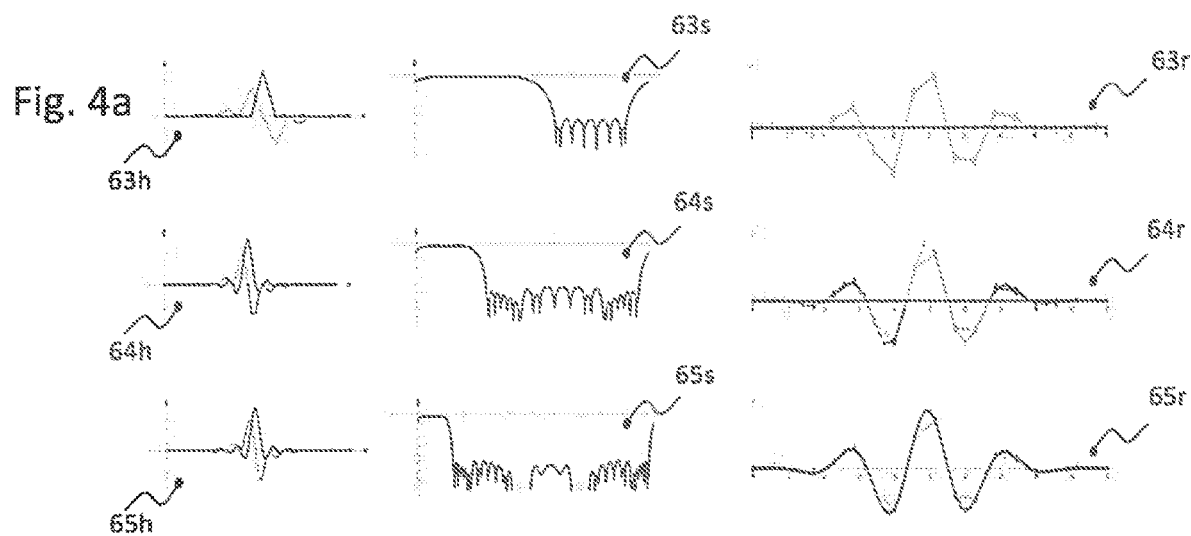
FIG. 4a shows a plot of, as an example of three complex impulse signals of three cascade complex interpolation stages, wherein the interpolation is performed around an I,Q Rf signal. The impulse signals and the spectra of each of the three interpolation stage are shown. And a signal interpolation example is shown.

To realize for example 8× up-sampling I,Q Rf interpolation in an very computational efficient manner, the interpolation is realized by a cascade of 3 up-sampling-interpolation-filters whereof each filter performs a 2× up-sampling, I,Q Rf based interpolation, utilized by means of complex bandpass filters 'cBpf' as indicate in FIG. 4c with 63, 64, 65 wherein the interpolation is performed around an I,Q Rf signal by means of, as an example, given complex impulse signals FIG. 4a indicated by 63h, 64h, 65k and the matching spectra 63s, 64s, 65s.

Figure 4B:
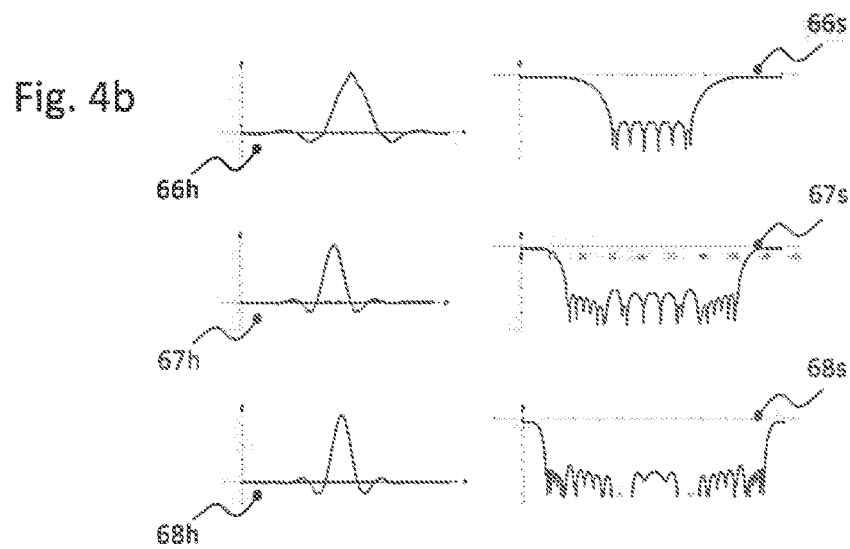
FIG. 4b shows a plot of, as an example of three impulse signals of three cascade interpolation stages, wherein the interpolation is performed around an Rx-signal, with fx=0. The impulse signals and the spectra of each of the three interpolation stage are shown.

To realize for example 8× up-sampling I,Q bb interpolation in an very computational efficient manner, the interpolation is realized by a cascade of 3 up-sampling-interpolation-filters whereof each filter performs a 2× up-sampling, I,Q bb based interpolation, utilized by means of complex low pass filters 'cLpf' in FIG. 4d as indicated by 66, 67, 68 wherein the interpolation is performed around an I,Q Rx signal with fx=0 by means of, as an example, given complex impulse signals FIG. 4b indicated by 66h, 67k, 68k and the matching spectra 66s, 67s, 68s.

An example of showing the cascade filters functionality, the up sampling filter results of the cascade filter embodiments 63, 64, 65 are shown, where 63r shows an example I-signal of the I-output of 63, the cascade filter 64, will in a first stage, transfer the signals of 63 to its output, in 64r the corresponding samples of 63r can be seen, then the filter 64 will in a second stage, present at its output, interpolated in between samples, as can be seen in 64r. The same is performed by the next filter 65 in the interpolating filter cascade, in 65r a smooth interpolated signal is shown. This is a signal with at least 16 samples per fc-cycle. In the case the frequency fc of the by 2 received signals are of a very low frequency, it might be that there are even too much samples per cycle. When the stages 31 (buffer length) might not be capable of handling this amount of data, then the high amount of samples per fc-cycle can be reduced, when the embodiment has placed by pass multiplexers 69 around the cascade interpolation filters. An example embodiment of a bypass for filter 63 is shown in FIG. 4c and indicated by 63, 69.

Figure 5A:
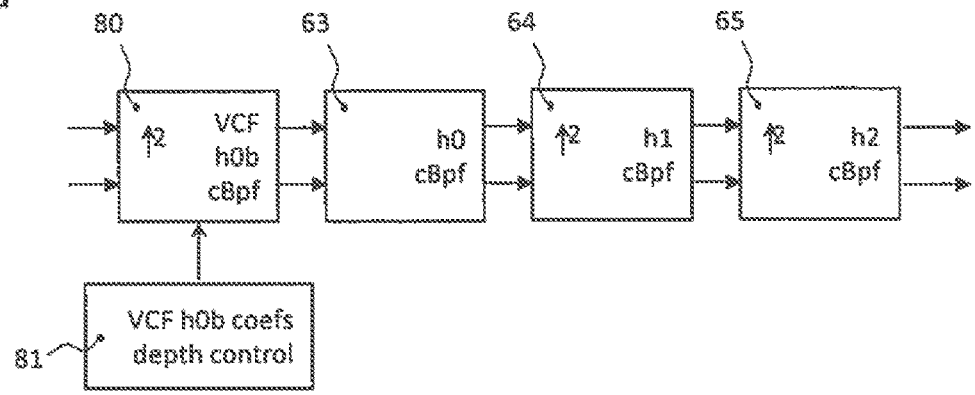
FIG. 5a shows a schematic illustration of the cascade interpolation, with the interpolation performed around I,Q Rf, as used in FIG. 4c), with the addition of a complex bandpass-filter h0b-cBpf, that, together with h0-cBpf, performs a depth dependent tracking filter (VCF) functionality.
Figure 5B:
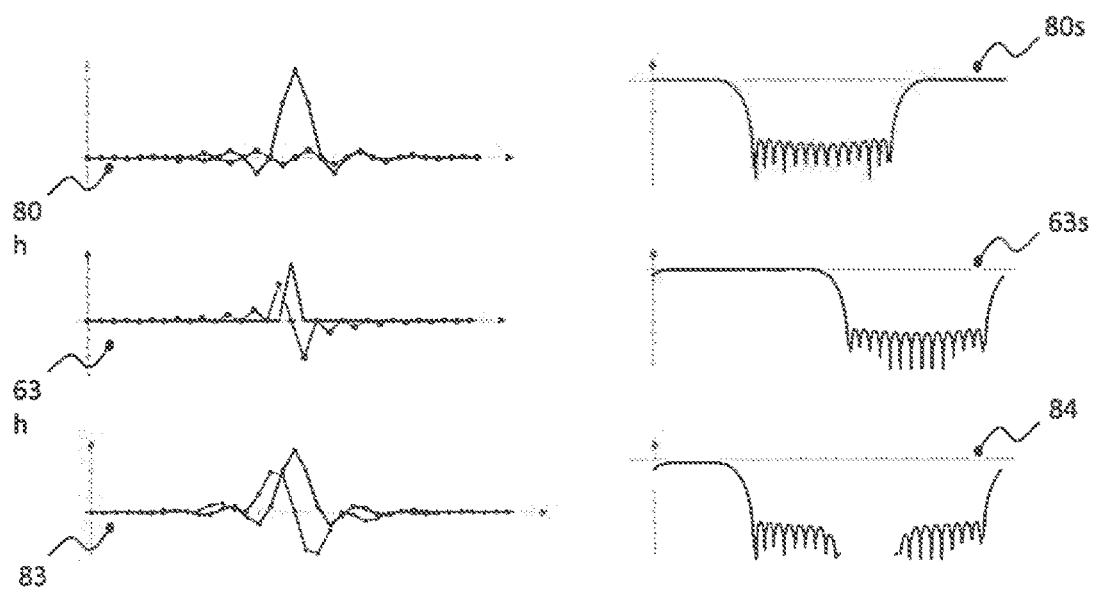
FIG. 5b shows a plot of the complex impulse responses, and the spectral transfer functions of h0b-cBpf and h0-cBpf, that work together to create, in addition to the interpolation, a depth dependent tracking filter functionality. The impulse response and the spectral transfer function of the convolution result of h0b-cBpf with h0-CBpf is also added to illustrate the narrowing of the complex bandpass, used for the depth dependent tracking filter functionality.

According to a further feature, as an extension to the cascade interpolation, an implementation of depth dependent tracking filter functionality (VCF), is provided. In FIG. 5a, a cascade interpolation embodiment is illustrated, with the added VCF, wherein the interpolation is performed around I,Q Rf. The first complex bandpass filter 80 up samples the input 2×, while the second filter 63 does not up sample. An example impulse response of 63 is given as FIG. 5b and indicated by 63h, and the corresponding spectral transfer function 63s clearly shows a wide bandpass around fc and it can be viewed that the spectral replica around 2×fc becomes suppressed, what realizes the interpolation functionality. Half of the filter coefficients of 63h, have a zero value, what makes the filter computational effective. The added filter 80 with the impulse response 80h as indicated in FIG. 5b and spectral transfer function 80s has the same wide pass-band bandwidth, as 63s, therefore also this filter is computational effective, because also for filter 80, half of the filter coefficients of 80h, have a zero value. The nonzero filter coefficients of 80h, become altered under the depth depending control 81, during the reception time. As shown in FIG. 5b 80s shows a situation at a certain receive depth/time, wherein, it can be viewed that 80s is a left shifted version of 63s, as a result of both filters 80, 63. The transfer function of the combined work of both the filters is shown is illustrated in FIG. 5b and indicated with 84. It can clearly be seen that it has both the functionalities, suppressing the spectral replica around 2×fc as interpolation functionality, and suppressing the higher frequencies of the ultrasound I,Q Rf signal content positioned around fc, as the VCF functionality. Also the resulting effective complex impulse response of the filters 80,63 is shown FIG. 5b and indicated with 83. This is a longer impulse response, due to the more narrow band width of 84, and therefore improving SNR during the reception of signals from deeper structures of the object O.

Figure 5C:
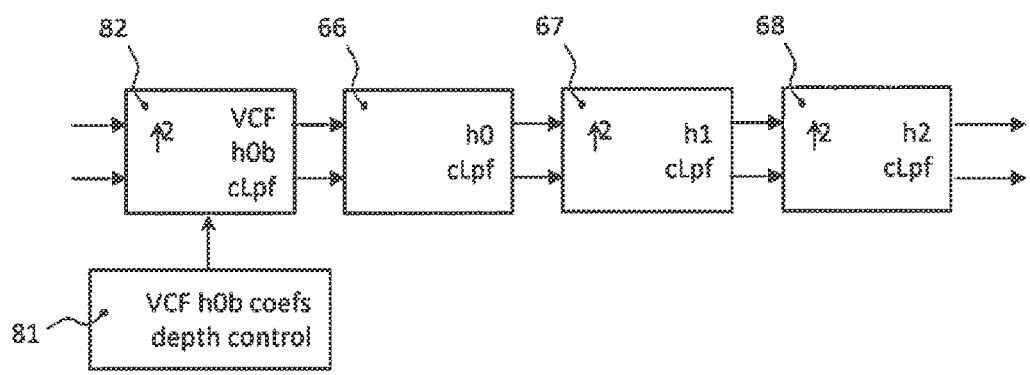
FIG. 5c shows a schematic illustration of an extension of the cascade interpolation, with the interpolation performed around fx=0, as used in FIG. 4d), with the addition of low pass filters with an impulse response h0b-cLpf that, together with h0-cLpf, can perform a depth dependent tracking filter (VCF) functionality.

FIG. 5c shows an embodiment of a cascade interpolation as used in FIG. 4d, with the added embodiment 82, as the implementation of depth dependent tracking filter functionality (VCF), intended for the preferred signal processing of the filters around fx=0. It functions in the same manner as the previously described embodiment of FIG. 5a, the transfer functions being just, in frequency shifted version of the ones shown in FIG. 5b.

The VCF functionality is also part of the I,Q-detection functionality, therefore the combination of the embodiment 60 according to FIG. 4c, and of the embodiment 80, 63 of FIG. 5a, are part of the detection-estimation D(t, Elm) prior to the beamforming. Therefore the added VCF functionality does not introduce internal beamforming distortion, as it relates to the formulation (3).

According to a further embodiment, traditional ultrasound systems might have a depth depending tracking filter functionality as indicated by 16 in FIG. 1b of some sort, that might be named differently as VCF, whereof it typically is performed at the output of the beamforming, where it could be positioned prior to the I,Q detection 8, or if it is realized in a complex manner, it might be located after the I,Q detection 8. In this traditional beamforming case the depth depending tracking filter (VCF) functionality, is therefore related to the equation (2), therefore the depth depending tracking filter (VCF) functionality, of this type of ultrasound embodiment, will also be afflicted, with internal signal-distortions.

Figure 6:
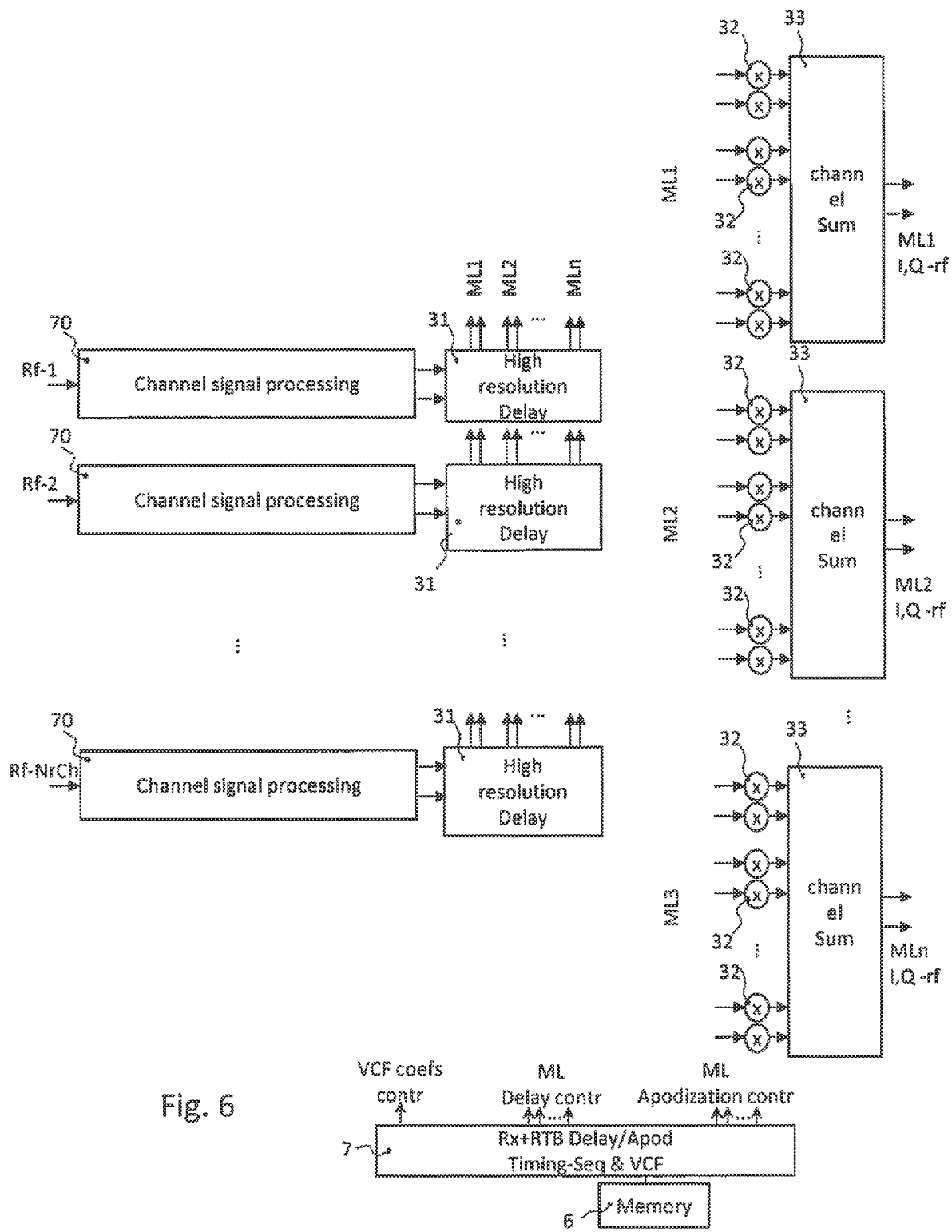
FIG. 6 shows a schematic illustration, being an overview, of a complete example embodiment of the multi-line I,Q Rf beamforming, with signal processing channels, including I,Q-detection and pre-computed I,Q interpolation, with a VCF option, to provide I,Q Rf-signals to the I,Q Rf beamforming functionality, consisting of, multi-line high resolution delay stages (with output decimation), multi-line apodization multipliers, and multi-line coherent element/channel summation. The multi-line high resolution delay, and the apodization stages are provided with beamforming control information, by a control block with a memory to distribute the receive delay information, and RTB-correction-delay information per element, and to distribute the receive apodization information per element.

FIG. 6 shows an example embodiment of a complete I,Q Rf, being configured to have RTB capability, multi-line dynamic receive focusing delay and sum beamforming according the present invention. The element/channel signal processing 70 might be substituted by embodiments as the ones disclosed according to FIGS. 3a, 3b, 3c, 3d). According to a further variant embodiments with a computational efficient methods as for example the one of FIG. 4c or 4d and between this two embodiments the one according to FIG. 4d is the most preferred one. The high resolution delay stage 31 consists of one I,Q samples-buffer that can hold a sufficient amount of up-sampled I,Q Rf samples to bridge the maximal need signal delay for the application. This I,Q sample buffer holds the undistorted I,Q-detected, VCF filtered and high quality interpolated up-sampled I,Q Rf samples, with at least 16 I,Q Rf samples per fc-cycle to ensure a beamforming result with a very low distortion and a high dynamic range. Since the stored I,Q Rf samples are at least a factor 8× oversampled, a wideband beamforming output channel can have a 8× decimation on the pre-computed I,Q Rf samples available in the buffer, therefore it can select a, one out of 8, nearest sample, to realize the fine delay resolution τdel(t, Elm) needed for beamforming. The receive and RTB, delay information is stored in the memory 6 and via 7 provide the buffer decimation readout circuits of 31 with the proper nearest delay to select a I,Q Rf sample, out of the buffer, to be further processed by the apodization/aperture weighing 32, where the apodization weighting values, are provided via 6 and 7. In this way a beamforming output for a MultiLine (MLx) becomes produced, after the channels summation 33, for that specific MLx beamforming output. Since, to produce many MLx beamforming of outputs, it is more efficient to pre-compute up sampled I,Q Rf samples when the upsample factor 'IpolFac' is lower than the amount of MultiLines 'NrML' that are needed to produce. Depending on the transmitted frequency fc, and for the active modality used bandwidth, several decimation/interpolation factors might be used.

According to an example the AFE decimators 62 of FIG. 4d reduce the sampling frequency Fsam used at the ADC 2, too $$\frac{Fsam}{M},$$

the cascade interpolation stages 82/66, 67, 68 up-sample the sampling frequency to $$\frac{Fsam}{M} \cdot 2^{NrCascadeStages},$$

(a cascade stage might be bypassed 69) and the decimation at the readout at 31 for a MLx output reduce the sampling frequency by a factor N to a output sample rate of:

$$\frac{Fsam}{M} \cdot 2^{NrCascadeStages} \cdot \frac{1}{N} = \frac{1}{M} \cdot \frac{2^{NrCascadeStages}}{N} \cdot Fsam$$

The preferred way of usage of the present invention, according to the equation (3), is to use a high as possible factor of M, (that realizes a optimal I,Q-detection estimation) given the signals bandwidth content, and to have the ratio of $$\frac{2^{NrCascadeStages}}{N}$$

set to, or near to, 1. Further it can be noted, that in a practical implementation of the present invention, the amount of Multi Lines that can be processed, can be higher in case the frequency fc and/or the signal content bandwidth is lower, this can be realized in practice as in that case a higher time-multiplexing-factor, can be utilized, starting at the read out of a multiline at the delay stages 31 and the following 32, 33 stages.

The beamforming technique of the present invention, shows that any means of detections, are preferred to be realized prior to the beamforming process itself, according to the equation (3). The computational efficient means of interpolation with pre-computation, can also be performed by any means of software processing, on any software capable device. Either, utilizing the computational efficient means of cascade interpolation, like for example in the embodiment of FIG. 5c, with, or without the VCF addition. Or utilizing some means of frequency domain processing. The interpolation pre-computation is independent of the beamforming process, and any I,Q detection filter can be utilized, it can be a I,Q detection filter for Echo-modality, or for Doppler-modality, it can even be I,Q detection/correlation modality filters that match with coded, or pulse-compression, transmissions. All these types of I,Q detecting filters, can be implemented in an over/up-sample manner. The pre-computed I,Q-detections results, D(t, Elm), might also be computed directly utilizing longer-taps complex filters. As these filters, filter the signals of each element, in axial/time direction independently, the pre-computed I,Q detection filtering needed for the active modality, can also be performed in frequency domain, as 1d-spectral signal processing for each probes-element. The (per element) processing steps might be, 1d time domain to frequency domain conversion of the by the AFE provided I,Q-bb samples of FIG. 3d) signals are around fx=0, then shifting the spectrum (in the frequency domain) to the fc position, then zero-stuff in frequency domain (equal to up-sampling), then convert back from frequency domain to time domain (to complete the interpolation), to produce the pre-computed I,Q-detection results, to be written into the high resolution delay buffers 31 of FIG. 6) now the time-domain beamforming can be completed. This means of frequency domain process of the beamforming is also suitable for other than linear array probes.

Figure 7:
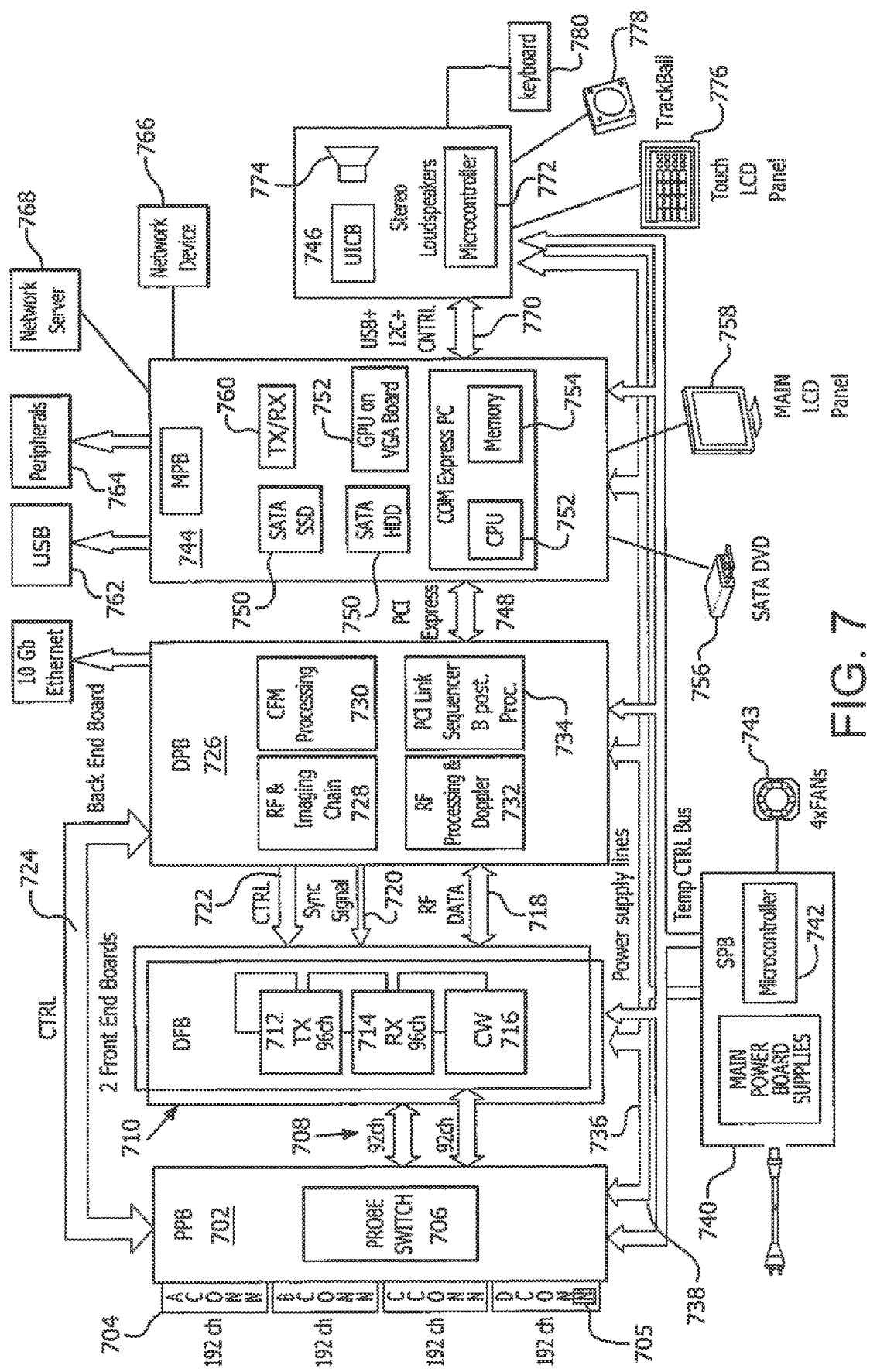
FIG. 7 illustrates a block diagram of an ultrasound system formed in accordance with an alternative embodiment.

FIG. 7 illustrates a block diagram of an ultrasound system formed in accordance with an alternative embodiment. The system of FIG. 7 implements the operations described herein in connection with various embodiments. By way of example, one or more circuits/processors within the system implement the operations of any processes illustrated in connection with the figures and/or described herein. The system includes a probe interconnect board 702 that includes one or more probe connection ports 704. The connection ports 704 may support various numbers of signal channels (e.g., 128, 192, 256, etc.). The connector ports 704 may be configured to be used with different types of probe arrays (e.g., phased array, linear array, curved array, 1D, 1.25D, 1.5D, 1.75D, 2D array, etc.). The probes may be configured for different types of applications, such as abdominal, cardiac, maternity, gynecological, urological and cerebrovascular examination, breast examination and the like.

One or more of the connection ports 704 may support acquisition of 2D image data and/or one or more of the connection ports 704 may support 3D image data. By way of example only, the 3D image data may be acquired through physical movement (e.g., mechanically sweeping or physician movement) of the probe and/or by a probe that electrically or mechanically steers the transducer array.

The probe interconnect board (PIB) 702 includes a switching circuit 706 to select between the connection ports 704. The switching circuit 706 may be manually managed based on user inputs. For example, a user may designate a connection port 704 by selecting a button, switch or other input on the system. Optionally, the user may select a connection port 704 by entering a selection through a user interface on the system.

Optionally, the switching circuit 706 may automatically switch to one of the connection ports 704 in response to detecting a presence of a mating connection of a probe. For example, the switching circuit 706 may receive a "connect" signal indicating that a probe has been connected to a selected one of the connection ports 704. The connect signal may be generated by the probe when power is initially supplied to the probe when coupled to the connection port 704. Additionally, or alternatively, each connection port 704 may include a sensor 705 that detects when a mating connection on a cable of a probe has been interconnected with the corresponding connection port 704. The sensor 705 provides signal to the switching circuit 706, and in response thereto, the switching circuit 706 couples the corresponding connection port 704 to PIB outputs 708. Optionally, the sensor 705 may be constructed as a circuit with contacts provided at the connection ports 704. The circuit remains open when no mating connected is joined to the corresponding connection port 704. The circuit is closed when the mating connector of a probe is joined to the connection port 704.

A control line 724 conveys control signals between the probe interconnection board 702 and a digital processing board 726. A power supply line 736 provides power from a power supply 740 to the various components of the system, including but not limited to, the probe interconnection board (PIB) 702, digital front end boards (DFB) 710, digital processing board (DPB) 726, the master processing board (MPB) 744, and a user interface control board (UICB) 746. A temporary control bus 738 interconnects, and provides temporary control signals between, the power supply 740 and the boards 702, 710, 726, 744 and 746. The power supply 740 includes a cable to be coupled to an external AC power supply. Optionally, the power supply 740 may include one or more power storage devices (e.g. batteries) that provide power when the AC power supply is interrupted or disconnected. The power supply 740 includes a controller 742 that manages operation of the power supply 740 including operation of the storage devices.

Additionally, or alternatively, the power supply 740 may include alternative power sources, such as solar panels and the like. One or more fans 743 are coupled to the power supply 740 and are managed by the controller 742 to be turned on and off based on operating parameters (e.g. temperature) of the various circuit boards and electronic components within the overall system (e.g. to prevent overheating of the various electronics).

The digital front-end boards 710 providing analog interface to and from probes connected to the probe interconnection board 702. The DFB 710 also provides pulse or control and drive signals, manages analog gains, includes analog to digital converters in connection with each receive channel, provides transmit beamforming management and receive beamforming management and vector composition (associated with focusing during receive operations).

The digital front end boards 710 include transmit driver circuits 712 that generate transmit signals that are passed over corresponding channels to the corresponding transducers in connection with ultrasound transmit firing operations. The transmit driver circuits 712 provide pulse or control for each drive signal and transmit beamforming management to steer firing operations to points of interest within the region of interest. By way of example, a separate transmit driver circuits 712 may be provided in connection with each individual channel, or a common transmit driver circuits 712 may be utilized to drive multiple channels. The transmit driver circuits 712 cooperate to focus transmit beams to one or more select points within the region of interest. The transmit driver circuits 712 may implement single line transmit, encoded firing sequences, multiline transmitter operations, generation of shear wave inducing ultrasound beams as well as other forms of ultrasound transmission techniques.

The digital front end boards 710 include receive beamformer circuits 714 that received echo/receive signals and perform various analog and digital processing thereon, as well as phase shifting, time delaying and other operations in connection with beamforming. The beam former circuits 714 may implement various types of beamforming, such as single-line acquisition, multiline acquisition as well as other ultrasound beamforming techniques.

The digital front end boards 710 include continuous wave Doppler processing circuits 716 configured to perform continuous wave Doppler processing upon received echo signals. Optionally, the continuous wave Doppler circuits 716 may also generate continuous wave Doppler transmit signals.

The digital front-end boards 710 are coupled to the digital processing board 726 through various buses and control lines, such as control lines 722, synchronization lines 720 and one or more data bus 718. The control lines 722 and synchronization lines 720 provide control information and data, as well as synchronization signals, to the transmit drive circuits 712, receive beamforming circuits 714 and continuous wave Doppler circuits 716. The data bus 718 conveys RF ultrasound data from the digital front-end boards 710 to the digital processing board 726. Optionally, the digital front end boards 710 may convert the RF ultrasound data to I,Q data pairs which are then passed to the digital processing board 726.

The digital processing board 726 includes an RF and imaging module 728, a color flow processing module 730, an RF processing and Doppler module 732 and a PCI link module 734. The digital processing board 726 performs RF filtering and processing, processing of black and white image information, processing in connection with color flow, Doppler mode processing (e.g. in connection with polls wise and continuous wave Doppler). The digital processing board 726 also provides image filtering (e.g. speckle reduction) and scanner timing control. The digital processing board 726 may include other modules based upon the ultrasound image processing functionality afforded by the system.

The modules 728-734 comprise one or more processors, DSPs, and/or FPGAs, and memory storing program instructions to direct the processors, DSPs, and/or FPGAs to perform various ultrasound image processing operations. The RF and imaging module 728 performs various ultrasound related imaging, such as B mode related image processing of the RF data. The RF processing and Doppler module 732 convert incoming RF data to I,Q data pairs, and performs Doppler related processing on the I, Q data pairs. Optionally, the imaging module 728 may perform B mode related image processing upon I, Q data pairs. The CFM processing module 730 performs color flow related image processing upon the ultrasound RF data and/or the I, Q data pairs. The PCI link 734 manages transfer of ultrasound data, control data and other information, over a PCI express bus 748, between the digital processing board 726 and the master processing board 744.

The master processing board 744 includes memory 750 (e.g. serial ATA solid-state devices, serial ATA hard disk drives, etc.), a VGA board 752 that includes one or more graphic processing unit (GPUs), one or more transceivers 760 one or more CPUs 752 and memory 754. The master processing board (also referred to as a PC board) provides user interface management, scan conversion and cine loop management. The master processing board 744 may be connected to one or more external devices, such as a DVD player 756, and one or more displays 758. The master processing board includes communications interfaces, such as one or more USB ports 762 and one or more ports 764 configured to be coupled to peripheral devices. The master processing board 744 is configured to maintain communication with various types of network devices 766 and various network servers 768, such as over wireless links through the transceiver 760 and/or through a network connection (e.g. via USB connector 762 and/or peripheral connector 764).

The network devices 766 may represent portable or desktop devices, such as smart phones, personal digital assistants, tablet devices, laptop computers, desktop computers, smart watches, ECG monitors, patient monitors, and the like. The master processing board 744 conveys ultrasound images, ultrasound data, patient data and other information and content to the network devices for presentation to the user. The master processing board 744 receives, from the network devices 766, inputs, requests, data entry and the like.

The network server 768 may represent part of a medical network, such as a hospital, a healthcare network, a third-party healthcare service provider, a medical equipment maintenance service, a medical equipment manufacturer, a government healthcare service and the like. The communications link to the network server 768 may be over the Internet, a private intranet, a local area network, a wide-area network, and the like.

The master processing board 744 is connected, via a communications link 770 with a user interface control board 746. The communications link 770 conveys data and information between the user interface and the master processing board 744. The user interface control board 746 includes one or more processors 772, one or more audio/video components 774 (e.g. speakers, a display, etc.). The user interface control board 746 is coupled to one or more user interface input/output devices, such as an LCD touch panel 776, a trackball 778, a keyboard 780 and the like. The processor 772 manages operation of the LCD touch panel 776, as well as collecting user inputs via the touch panel 776, trackball 778 and keyboard 780, where such user inputs are conveyed to the master processing board 744 in connection with implementing embodiments herein.

Figure 8:
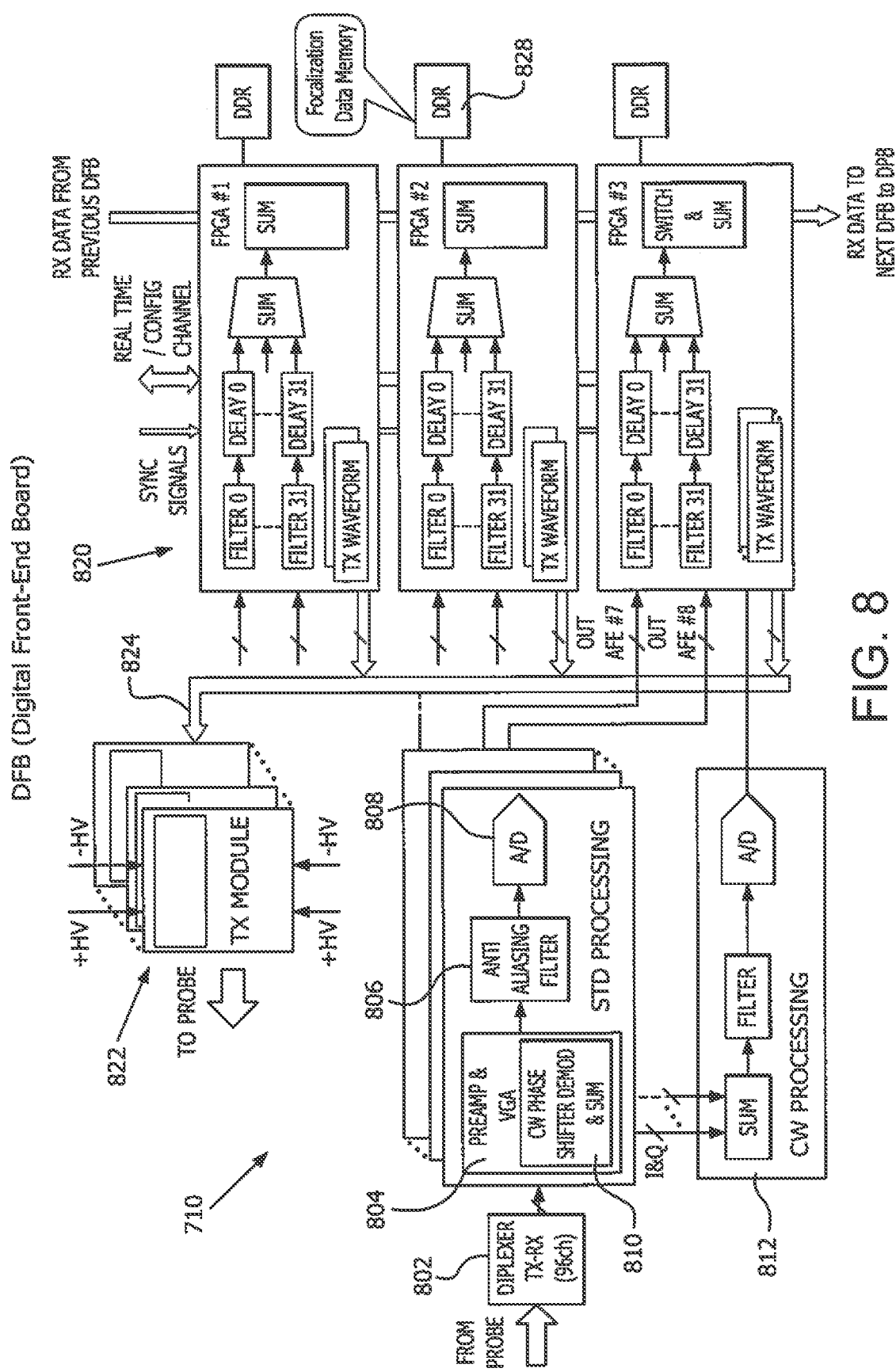
FIG. 8 illustrates a block diagram of a portion of the digital front-end boards.

FIG. 8 illustrates a block diagram of a portion of the digital front-end boards 710 formed in accordance with embodiments herein. A group of diplexers 802 receive the ultrasound signals for the individual channels over the PIB output 708. The ultrasound signals are passed along a standard processing circuit 805 or to a continuous wave processing circuit 812, based upon the type of probing utilized. When processed by the standard processing circuit 805, a preamplifier and variable gain amplifier 804 process the incoming ultrasound receive signals that are then provided to an anti-aliasing filter 806 which performs anti-aliasing filtering.

According to an embodiment the retrospective transmit beam focusing according to the present invention may be applied to the RF data directly acquired by the system or to transformed data according to different transformations as for example as a phase/quadrature (I/Q) transformation, or similar.

In the embodiment of FIG. 8 an example of the said transformation of the RF data is disclosed According to this example, the output of the filter 806 is provided to an A/D converter 808 that digitizes the incoming analog ultrasound receive signals. When a continuous wave (CW) probe is utilized, the signals therefrom are provided to a continuous wave phase shifter, demodulator and summer 810 which converts the analog RF receive signals to I,Q data pairs. The CW I,Q data pairs are summed, filtered and digitized by a continuous wave processing circuit 812. Outputs from the standard or continuous wave processing circuits 805, 812 are then passed to beam forming circuits 820 which utilize one or more FPGAs to perform filtering, delaying and summing the incoming digitized receive signals before passing the RF data to the digital processing board 826 (FIG. 7). The FPGAs receive focalization data from memories 828. The focalization data is utilized to manage the filters, delays and summing operations performed by the FPGAs in connection with beamforming. The beamformed RF or I/Q data is passed between the beamforming circuits 820 and ultimately to the digital processing board 726.

The digital front-end boards 710 also include transmit modules 822 that provide transmit drive signals to corresponding transducers of the ultrasound probe. The beamforming circuits 820 include memory that stores transmit waveforms. The transmit modules 822 receive transmit waveforms over line 824 from the beamforming circuits 820.

Figure 9:
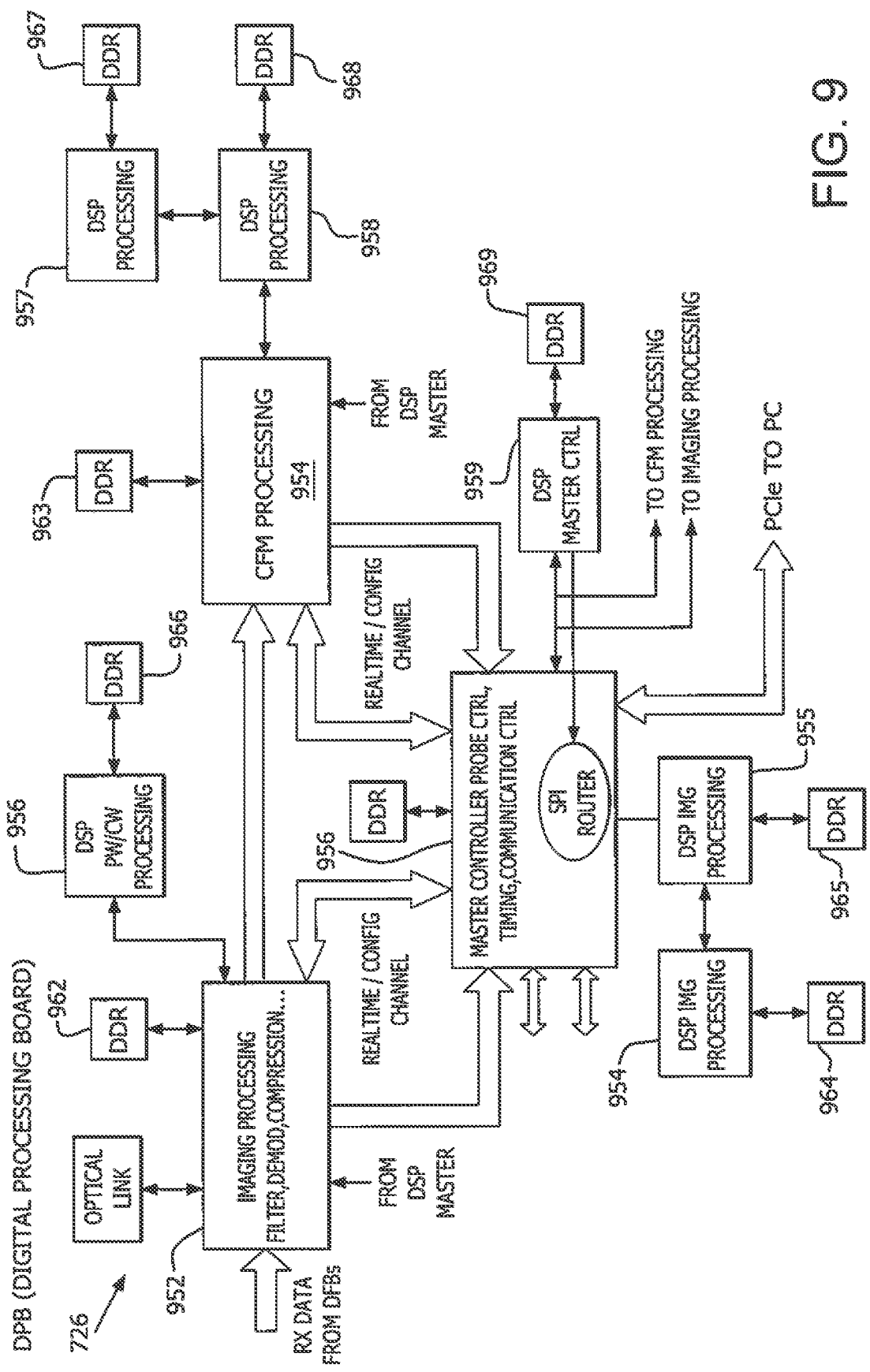
FIG. 9 illustrates a block diagram of the digital processing board.

FIG. 9 illustrates a block diagram of the digital processing board 726 implemented in accordance with embodiments herein. The digital processing board 726 includes various processors 952-959 to perform different operations under the control of program instructions saved within corresponding memories see 962-969. A master controller 950 manages operation of the digital processing board 726 and the processors 952-959. By way of example, one or more processors as the 952 may perform filtering, the modulation, compression and other operations, while another processor 953 performs color flow processing. The master controller provides probe control signals, timing control signals, communications control and the like. The master controller 950 provides real-time configuration information and synchronization signals in connection with each channel to the digital front-end board 710.

It should be clearly understood that the various arrangements and processes broadly described and illustrated with respect to the FIGS., and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the FIGS., which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally or alternatively, the controllers and the controller device may represent circuitry that may be implemented as hardware. The above examples are exemplary only, and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A method for performing a distortion free multi line receive focusing beamforming of ultrasound signals, comprising:
   transmitting transmit beams around a transmitted center frequency fc from an array transducer comprising a certain number of transducer elements to a target;
   receiving echo signals from at least part of the transducer elements of the array transducer;
   obtaining receive signals from each of the said transducer elements of an array transducer;
   processing the receive signals to obtain complex detected signals having in-phase (I) and quadrature (Q) components around the transmitted center frequency fc;
   carrying out delay and sum beamforming of the complex detected signal components of each transducer element.

2. Method according to claim 1, wherein complex detected signals are obtained by:
   shifting the spectral content of the receive signals by (fc−fx) to obtain intermediate signals, where fx is a predetermined working frequency;
   up sampling the intermediate signals by complex interpolation filters to obtain interpolated intermediate signals; and
   shifting the spectral content of the interpolated intermediate signals by (fx−fc).

3. A method according to claim 2, wherein the working frequency fx is set to 0 so that the intermediate signals are base band signals.

4. Method according to claim 2, wherein, depending on the signals bandwidth, a decimation on the complex detected signals is performed.

5. A method for performing a distortion free multi line receive focusing beamforming of ultrasound signals, comprising:
   transmitting transmit beams around a transmitted center frequency fc from an array transducer comprising a certain number of transducer elements to a target;
   receiving echo signals from at least part of the transducer elements of the array transducer;
   obtaining receive signals from transducer elements of an ultrasound probe;
   processing the receive signals, prior to a delay section, to obtain complex detected signals having in-phase (I) and quadrature (Q) components;
   up-sampling the complex detected signals to obtain complex interpolated I,Q-Rf signals with high-time-resolution;
   applying time delay and decimation on the complex interpolated I,Q-Rf signals with high-time-resolution, to form delayed complex I,Q-Rf signals around the transmitted center frequency fc;
   summing, in a coherent manner, the delayed complex I,Q-Rf signals to produce a dynamic focus receive beamforming output,
   wherein up-sampling the complex detected signals comprises applying complex interpolators in a cascade chain, with or without a depth dependent tracking filter VCF.

6. Method according to claim 5, wherein the interpolated I,Q Rf signals with high-time-resolution, are obtained by means of up sampled, I,Q interpolation, using a plurality of complex interpolators in a cascade chain, to realize a higher time-delay resolution, with at least eight I,Q samples per fc-cycle.

7. A method for performing a distortion free multi line receive focusing beamforming of ultrasound signals, comprising:
   transmitting transmit beams around a transmitted center frequency fc from an array transducer comprising a certain number of transducer elements to a target;
   receiving signals by each transducer element;
   converting the received signals to complex signals having in-phase (I) and quadrature (Q) components;
   applying complex signal modulation for shifting the signal spectral content in frequency of the complex signals from the transmitted center frequency fc to a working frequency (fx) to obtain intermediate complex signals;
   bandpass filtering the intermediate complex signals around the working frequency fx for passing only the spectral content of the complex signals around the said working frequency fx;
   shifting back the spectral content of the filtered intermediate complex signal around the working frequency (fx) to the transmitted center frequency fc;
   generating higher amount of samples with a finer delay-resolution by a complex interpolation of the complex signal with the spectral content shifted back to the transmitted center frequency fc by complex interpolation filtering with a wideband passband filter;
   providing high resolution delay samples of the complex signal with the spectral content shifted back to transmitted center frequency fc, each sample corresponding to finer delay-resolution than the initially sampled received signals before the step of conversion to a complex receive signals;
choosing among the samples those having the most appropriate high resolution delay;
carrying out delay and sum beamforming.

8. Method for performing a distortion free multi line receive focusing beamforming of ultrasound signals, comprising:
transmitting transmit beams around a transmitted center frequency fc from an array transducer comprising a certain number of transducer elements to a target;
receiving signals by each transducer element;
converting the received signals to complex signals having in-phase (I) and quadrature (Q) components;
applying complex signal modulation for shifting the signal spectral content in frequency of the complex signals from the transmitted center frequency fc to a working frequency ix to obtain intermediate complex signals;
bandpass filtering the intermediate complex signals around the working frequency fx for passing only the spectral content around the said working frequency fx;
generating higher amount of samples with a finer delay-resolution by a complex interpolation of the complex signal with the spectral content shifted at the working frequency (fx) by complex interpolation filtering with a wideband passband filter;
shifting back the spectral content of the complex signal around the working frequency (fx) to the transmitted center frequency fc;
providing high resolution delay samples of the complex signal with the spectral content shifted back to the transmitted center frequency fc each sample corresponding to finer delay-resolution than the initially sampled received signals before the step of conversion to a complex receive signal;
choosing among the samples those having the most appropriate high resolution delay;
carrying out delay and sum beamforming.

9. Method according to claim 7, wherein the frequency shift is set as the difference of the working frequency and the original transmitted center frequency fc, namely (fx−fc) and fx is chosen as 0, determining a frequency shift of −fc from the transmitted center frequency to the base band frequency and vice versa at the two shifting and back-shifting steps.

10. Method according to claim 7, characterized in being provided in combination with a retrospective dynamic transmit focusing beamforming RTB technique and in which after choosing the appropriate complex signal sample shifted back at the original transmit center frequency and corresponding to a certain high resolution fine delay, to the said signal the corresponding beamforming delay and optionally the RTB delays and apodization weights are applied before coherent summation with the other samples complex signals determined from the received signals of the other transducer elements.

11. An ultrasound system, comprising:
an ultrasound probe including an array of transducer elements transforming electric input signals in acoustic transmit signals and transforming acoustic echo signals in electric receive signals;
a transmit beamformer generating the driving input signals for the transducer elements according to a transmit scheme for driving the transducer array to transmit a plurality of transmit beams from an array transducer;
the transmit beamformer including a memory configured to store time delays to synchronize contributions of transmit signals of the transducer elements of the array according to the said transmission scheme;
a receive beamformer including a receive signals processing unit configured to process the echo signals received in response to the transmit beams to produce a plurality of receive lines of echo signals;
a focalization delay module which applies to each receive signal contribution of each channel or transducer element the corresponding focalization delay for re-aligning the time of arrival of the receive signal contributions at the transducer elements of the transducer array from each reflecting or focus point;
an image generation unit producing an image producing using the said line image data;
a complex demodulator, with bandwidth limiting filters, and with a decimation capability, as complex detection of the receive signals from each transducer element to generate I,Q detected complex receive signals;
an up sampling complex interpolation filter unit of each I,Q detected complex receive signals, to generate I,Q detected receive signals with high time resolution;
a memory to store receive focus time delays in connection with a plurality of receive elements;
the said a complex demodulator, the said up sampling complex interpolation filters and the said memory being provided between an input of the Rf receive signals of each transducer element and the input of the focalization module;
the focalization module further comprising an I,Q Rf delay buffer, to temporary hold the I,Q Rf receive signals with high time resolution, to apply time delays to form delayed I,Q Rf receive signals and sum, in a coherent manner, the delayed I,Q Rf signals to obtain focused receive I,Q Rf beamformer output.

12. An ultrasound system according to claim 11, characterized in that it comprises a multiline beamformer and particularly a retrospective dynamic transmit focusing beamformer, the said multiline beamformers comprising a multiline processor for each receive line encompassed by the aperture or the width of each transmit beam centered on a certain transmit line position.

13. An ultrasound system according to claim 11, characterized in that the complex demodulator with bandwidth limiting filters operates as a carrier frequency converter or shifter of the spectral content of the complex receive signals (I,Q) at the carrier frequency of the transmit beam to a different carrier frequency (fx),
a complex multiplier as a converter, to convert the I,Q detected receive signals with high time resolution, with a working carrier frequency (fx), to complex signals (I,Q-Rf) with high time resolution, with the original ultrasound carrier frequency fc, following the complex signal (I,Q) interpolation filter unit.

14. An ultrasound system according to claim 11, characterized in that the I,Q Rf delay buffer readout, is configured to perform decimation on the I,Q Rf signals to be coherently summed, to produce an I,Q Rf beamformer output.

15. An ultrasound system according to claim 11, characterized in that the complex signal (I,Q) interpolation filter unit comprises a cascade of up sampling complex interpolation filters generating I,Q detected receive signal samples with high time resolution.

16. An ultrasound system according to claim 15, characterized in that the cascade interpolation filter is a wide-band filter with a plurality of zero filter coefficients.

17. An ultrasound system according to claim 15, characterized in that there is provided an interpolation filter unit, or a cascade interpolation chain with a depth dependent tracking filter (VCF) functionality, wherein the nonzero filter coefficients, become altered under a depth depending control by the said depth dependent tracking filter.

18. A beamforming processor comprising:
- a receive signals processing unit configured to process the echo signals received in response to the transmit beams to produce a plurality of receive lines of echo signals;
- a focalization delay module which applies to each receive signal contribution of each channel or transducer element the corresponding focalization delay for re-aligning the time of arrival of the receive signal contributions at the transducer elements of the transducer array from each reflecting or focus point;
- an image generation unit producing an image producing using the said line image data;
- a complex demodulator, with bandwidth limiting Filters, and with a decimation capability, as complex detection of the receive signals from each transducer element to generate I,Q detected complex receive signals;
- an up sampling complex interpolation filter unit of each I,Q detected complex receive signals, to generate I,Q detected receive signals with high time resolution;
- a memory to store receive focus time delays in connection with a plurality of receive elements;
- the said a complex demodulator, the said up sampling complex interpolation filters and the said memory being provided between an input of the Rf receive signals of each transducer element and the input of the focalization module;
- the focalization module further comprising an I,Q Rf delay buffer, to temporary hold the I,Q Rf receive signals with high time resolution, to apply time delays to form delayed I,Q Rf receive signals and sum, in a coherent manner, the delayed I,Q Rf signals to obtain focused receive I,Q Rf beamformer output.

19. A beamforming processor according to claim 18, wherein said beamformer processor is a multiline beamformer and particularly a retrospective dynamic transmit focusing beamformer, the said multiline beamformers comprising a multiline processor for each receive line encompassed by the aperture or the width of each transmit beam centered on a certain transmit line position.

* * * * *